United States Patent
Taniguchi et al.

(10) Patent No.: US 7,045,298 B2
(45) Date of Patent: *May 16, 2006

(54) METHOD FOR IDENTIFYING OR SCREENING AGONIST AND ANTAGONIST TO PPAR

(75) Inventors: Tomoyasu Taniguchi, Toda (JP); Junko Mizukami, Ootsu (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 367 days.

This patent is subject to a terminal disclaimer.

(21) Appl. No.: 10/109,886

(22) Filed: Apr. 1, 2002

(65) Prior Publication Data

US 2002/0119499 A1 Aug. 29, 2002

Related U.S. Application Data

(63) Continuation of application No. 09/514,247, filed on Feb. 28, 2000, now Pat. No. 6,365,361, which is a continuation-in-part of application No. PCT/JP98/03734, filed on Aug. 24, 1998.

(30) Foreign Application Priority Data

Aug. 27, 1997 (JP) .................................. 9-231084

(51) Int. Cl.
*G01N 33/53* (2006.01)
*G01N 33/567* (2006.01)

(52) U.S. Cl. .......................................... 435/7.1; 435/7.2

(58) Field of Classification Search .................. 435/7.1, 435/7.2, 7.8
See application file for complete search history.

(56) References Cited

U.S. PATENT DOCUMENTS

| 5,283,173 A | 2/1994 | Fields et al. |
| 6,689,574 B1 * | 2/2004 | Cummings et al. .......... 435/7.8 |

OTHER PUBLICATIONS

Zhu Y, et al. J. Biol. Chem. 272(41):25500-25506, 1997.*
Elbrecht A, et al. BBRC. 224:431-437, 1996.*
Mizukami J, et al. BBRC. 240:61-64, 1997.*
Krey, "Fatty acids, eicosandoids, and hypolipidemic agents idenfified as ligands of peroxisome proliferator-activiated receptors by coactiviator-depsndent receptor ligand assay", *Molecular Endocrinology*, 11(6):779-791 (1997).
Mizukami et al., "The antidiabetic agent thiazolidinedione stimulates the interaction between PPARy and CBP" *Biochem. Biophys. Res. Comm.*, 240:81-84, (1997).
Zhu et al., "Cloning and Identification of mouse steroid receptor coactivators-1 (mSRC-1), as a coactivators of peroxisome proliferator-activated receptor gamma", *Gene Expression*, 6:185-195 (1996).
Elberecht et al., Molecular cloning, expression and characterization of human peroxisome prolifereator activated receptors gamma 1 and gamma2. *Biochem. Biohys. Res. Comm.*, 224:431-437 (1996).

* cited by examiner

*Primary Examiner*—Robert S. Landsman
(74) *Attorney, Agent, or Firm*—Browdy and Neimark

(57) ABSTRACT

A method for identifying or screening an agonist for or antagonist to a peroxisome proliferator activated receptor (PPAR) which comprises allowing a test cell and a substance to be tested to coexist, and detecting a change in a ligand-dependent interaction between the PPAR and a coactivator in the test cells due to the substance to be tested by measuring the expression of a reporter gene as an index.

9 Claims, 3 Drawing Sheets

SEQUENCE LISTING

<160> NUMBER OF SEQ ID NOS: 10

<210> SEQ ID NO 1
<211> LENGTH: 35

-continued

```
<212> TYPE: DNA
<213> ORGANISM: Artificial Sequence
<220> FEATURE:
<223> OTHER INFORMATION: Artificially synthesized primer sequence

<400> SEQUENCE: 1
tcccccgggt gctgttatgg gtgaaactct gggag                              35

<210> SEQ ID NO 2
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 2
ccgctcgaga aatgttggca gtggctcagg actct                              35

<210> SEQ ID NO 3
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 3
cgggatccgt atggccgaga acttgctgga cggac                              35

<210> SEQ ID NO 4
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 4
gaagatcttc tctgttgccc tgcaccaaca gaacc                              35

<210> SEQ ID NO 5
<211> LENGTH: 1679
<212> TYPE: DNA
<213> ORGANISM: Homo sapiens
<220> FEATURE:
<221> NAME/KEY: CDS
<222> LOCATION: (159)..(1679)

<400> SEQUENCE: 5
gccagaacca ccgcacgatg ttgctgtcgg ccacacagtg cttcagcagc gtgttcgact    60
tccagtcgtt caagtctttt cttttcacgg attgatcttt tgctagatag agacaaaata   120
tcagtgtgaa ttacagcaaa cccctattcc atgctgtt atg ggt gaa act ctg gga   176
                                          Met Gly Glu Thr Leu Gly
                                            1               5 gat tct cct att gac cca gaa agc gat tcc ttc act gat aca ctg tct     224
Asp Ser Pro Ile Asp Pro Glu Ser Asp Ser Phe Thr Asp Thr Leu Ser
         10                  15                  20 gca aac ata tca caa gaa atg acc atg gtt gac aca gag atc gca ttc     272
Ala Asn Ile Ser Gln Glu Met Thr Met Val Asp Thr Glu Ile Ala Phe
     25                  30                  35 tgg ccc acc aac ttt ggg atc agc tcc gtg gat ctc tcc gta atg gaa     320
Trp Pro Thr Asn Phe Gly Ile Ser Ser Val Asp Leu Ser Val Met Glu
 40                  45                  50 gac cac tcc cac tcc ttt gat atc aag ccc ttc act act gtt gac ttc     368
Asp His Ser His Ser Phe Asp Ile Lys Pro Phe Thr Thr Val Asp Phe
55                  60                  65                  70
```

```
tcc agc att tct act cca cat tac gaa gac att cca ttc aca aga aca      416
Ser Ser Ile Ser Thr Pro His Tyr Glu Asp Ile Pro Phe Thr Arg Thr
            75                  80                  85 gat cca gtg gtt gca gat tac aag tat gac ctg aaa ctt caa gag tac      464
Asp Pro Val Val Ala Asp Tyr Lys Tyr Asp Leu Lys Leu Gln Glu Tyr
        90                  95                 100 caa agt gca atc aaa gtg gag cct gca tct cca cct tat tat tct gag      512
Gln Ser Ala Ile Lys Val Glu Pro Ala Ser Pro Pro Tyr Tyr Ser Glu
            105                 110                 115 aag act cag ctc tac aat aag cct cat gaa gag cct tcc aac tcc ctc      560
Lys Thr Gln Leu Tyr Asn Lys Pro His Glu Glu Pro Ser Asn Ser Leu
        120                 125                 130 atg gca att gaa tgt cgt gtc tgt gga gat aaa gct tct gga ttt cac      608
Met Ala Ile Glu Cys Arg Val Cys Gly Asp Lys Ala Ser Gly Phe His
135                 140                 145                 150 tat gga gtt cat gct tgt gaa gga tgc aag ggt ttc ttc cgg aga aca      656
Tyr Gly Val His Ala Cys Glu Gly Cys Lys Gly Phe Phe Arg Arg Thr
            155                 160                 165 atc aga ttg aag ctt atc tat gac aga tgt gat ctt aac tgt cgg atc      704
Ile Arg Leu Lys Leu Ile Tyr Asp Arg Cys Asp Leu Asn Cys Arg Ile
        170                 175                 180 cac aaa aaa agt aga aat aaa tgt cag tac tgt cgg ttt cag aaa tgc      752
His Lys Lys Ser Arg Asn Lys Cys Gln Tyr Cys Arg Phe Gln Lys Cys
            185                 190                 195 ctt gca gtg ggg atg tct cat aat gcc atc agg ttt ggg cgg atc gca      800
Leu Ala Val Gly Met Ser His Asn Ala Ile Arg Phe Gly Arg Ile Ala
        200                 205                 210 cag gcc gag aag gag aag ctg ttg gcg gag atc tcc agt gat atc gac      848
Gln Ala Glu Lys Glu Lys Leu Leu Ala Glu Ile Ser Ser Asp Ile Asp
215                 220                 225                 230 cag ctc aat cca gag tcc gct gac ctc cgt cag gcc ctg gca aaa cat      896
Gln Leu Asn Pro Glu Ser Ala Asp Leu Arg Gln Ala Leu Ala Lys His
            235                 240                 245 ttg tat gac tca tac ata aag tcc ttc ccg ctg acc aaa gca aag gcg      944
Leu Tyr Asp Ser Tyr Ile Lys Ser Phe Pro Leu Thr Lys Ala Lys Ala
        250                 255                 260 agg gcg atc ttg aca gga aag aca aca gac aaa tca cca ttc gtt atc      992
Arg Ala Ile Leu Thr Gly Lys Thr Thr Asp Lys Ser Pro Phe Val Ile
            265                 270                 275 tat gac atg aat tcc tta atg atg gga gaa gat aaa atc aag ttc aaa     1040
Tyr Asp Met Asn Ser Leu Met Met Gly Glu Asp Lys Ile Lys Phe Lys
        280                 285                 290 cac atc acc ccc ctg cag gag cag agc aaa gag gtg gcc atc cgc atc     1088
His Ile Thr Pro Leu Gln Glu Gln Ser Lys Glu Val Ala Ile Arg Ile
295                 300                 305                 310 ttt cag ggc tgc cag ttt cgc tcc gtg gag gct gtg cag gag atc aca     1136
Phe Gln Gly Cys Gln Phe Arg Ser Val Glu Ala Val Gln Glu Ile Thr
            315                 320                 325 gag tat gcc aaa agc att cct ggt ttt gta aat ctt gac ttg aac gac     1184
Glu Tyr Ala Lys Ser Ile Pro Gly Phe Val Asn Leu Asp Leu Asn Asp
        330                 335                 340 caa gta act ctc ctc aaa tat gga gtc cac gag atc att tac aca atg     1232
Gln Val Thr Leu Leu Lys Tyr Gly Val His Glu Ile Ile Tyr Thr Met
            345                 350                 355 ctg gcc tcc ttg atg aat aaa gat ggg gtt ctc ata tcc gag ggc caa     1280
Leu Ala Ser Leu Met Asn Lys Asp Gly Val Leu Ile Ser Glu Gly Gln
        360                 365                 370 ggc ttc atg aca agg gag ttt cta aag agc ctg cga aag cct ttt ggt     1328
Gly Phe Met Thr Arg Glu Phe Leu Lys Ser Leu Arg Lys Pro Phe Gly
```

|  |  |  |  |  |  |  |  |  |  |  |  |  |  |  |  |      |
|---|---|---|---|---|---|---|---|---|---|---|---|---|---|---|---|------|
|  |  |  | 375 |  |  |  | 380 |  |  |  | 385 |  |  |  | 390 |  |
| gac | ttt | atg | gag | ccc | aag | ttt | gag | ttt | gct | gtg | aag | ttc | aat | gca | ctg | 1376 |
| Asp | Phe | Met | Glu | Pro | Lys | Phe | Glu | Phe | Ala | Val | Lys | Phe | Asn | Ala | Leu |  |
|  |  |  |  | 395 |  |  |  | 400 |  |  |  | 405 |  |  |  |  |
| gaa | tta | gat | gac | agc | gac | ttg | gca | ata | ttt | att | gct | gtc | att | att | ctc | 1424 |
| Glu | Leu | Asp | Asp | Ser | Asp | Leu | Ala | Ile | Phe | Ile | Ala | Val | Ile | Ile | Leu |  |
|  |  |  |  | 410 |  |  |  | 415 |  |  |  | 420 |  |  |  |  |
| agt | gga | gac | cgc | cca | ggt | ttg | ctg | aat | gtg | aag | ccc | att | gaa | gac | att | 1472 |
| Ser | Gly | Asp | Arg | Pro | Gly | Leu | Leu | Asn | Val | Lys | Pro | Ile | Glu | Asp | Ile |  |
|  |  |  | 425 |  |  |  | 430 |  |  |  | 435 |  |  |  |  |  |
| caa | gac | aac | ctg | cta | caa | gcc | ctg | gag | ctc | cag | ctg | aag | ctg | aac | cat | 1520 |
| Gln | Asp | Asn | Leu | Leu | Gln | Ala | Leu | Glu | Leu | Gln | Leu | Lys | Leu | Asn | His |  |
|  |  | 440 |  |  |  | 445 |  |  |  | 450 |  |  |  |  |  |  |
| cct | gag | tcc | tca | cag | ctg | ttt | gcc | aag | ctg | ctc | cag | aaa | atg | aca | gac | 1568 |
| Pro | Glu | Ser | Ser | Gln | Leu | Phe | Ala | Lys | Leu | Leu | Gln | Lys | Met | Thr | Asp |  |
| 455 |  |  |  |  | 460 |  |  |  |  | 465 |  |  |  | 470 |  |  |
| ctc | aga | cag | att | gtc | acg | gaa | cac | gtg | cag | cta | ctg | cag | gtg | atc | aag | 1616 |
| Leu | Arg | Gln | Ile | Val | Thr | Glu | His | Val | Gln | Leu | Leu | Gln | Val | Ile | Lys |  |
|  |  |  |  | 475 |  |  |  | 480 |  |  |  | 485 |  |  |  |  |
| aag | acg | gag | aca | gac | atg | agt | ctt | cac | ccg | ctc | ctg | cag | gag | atc | tac | 1664 |
| Lys | Thr | Glu | Thr | Asp | Met | Ser | Leu | His | Pro | Leu | Leu | Gln | Glu | Ile | Tyr |  |
|  |  |  | 490 |  |  |  | 495 |  |  |  | 500 |  |  |  |  |  |
| aag | gac | ttg | tac | tag |  |  |  |  |  |  |  |  |  |  |  | 1679 |
| Lys | Asp | Leu | Tyr |  |  |  |  |  |  |  |  |  |  |  |  |  |
|  |  | 505 |  |  |  |  |  |  |  |  |  |  |  |  |  |  |

<210> SEQ ID NO 6
<211> LENGTH: 506
<212> TYPE: PRT
<213> ORGANISM: Homo sapiens

<400> SEQUENCE: 6

| Met | Gly | Glu | Thr | Leu | Gly | Asp | Ser | Pro | Ile | Asp | Pro | Glu | Ser | Asp | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Thr | Asp | Thr | Leu | Ser | Ala | Asn | Ile | Ser | Gln | Glu | Met | Thr | Met | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Thr | Glu | Ile | Ala | Phe | Trp | Pro | Thr | Asn | Phe | Gly | Ile | Ser | Ser | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Leu | Ser | Val | Met | Glu | Asp | His | Ser | His | Ser | Phe | Asp | Ile | Lys | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Phe | Thr | Thr | Val | Asp | Phe | Ser | Ser | Ile | Ser | Thr | Pro | His | Tyr | Glu | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Pro | Phe | Thr | Arg | Thr | Asp | Pro | Val | Val | Ala | Asp | Tyr | Lys | Tyr | Asp |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Lys | Leu | Gln | Glu | Tyr | Gln | Ser | Ala | Ile | Lys | Val | Glu | Pro | Ala | Ser |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Pro | Pro | Tyr | Tyr | Ser | Glu | Lys | Thr | Gln | Leu | Tyr | Asn | Lys | Pro | His | Glu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Glu | Pro | Ser | Asn | Ser | Leu | Met | Ala | Ile | Glu | Cys | Arg | Val | Cys | Gly | Asp |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Lys | Ala | Ser | Gly | Phe | His | Tyr | Gly | Val | His | Ala | Cys | Glu | Gly | Cys | Lys |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Gly | Phe | Phe | Arg | Arg | Thr | Ile | Arg | Leu | Lys | Leu | Ile | Tyr | Asp | Arg | Cys |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | Leu | Asn | Cys | Arg | Ile | His | Lys | Lys | Ser | Arg | Asn | Lys | Cys | Gln | Tyr |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Cys | Arg | Phe | Gln | Lys | Cys | Leu | Ala | Val | Gly | Met | Ser | His | Asn | Ala | Ile |

```
            195                 200                 205
Arg Phe Gly Arg Ile Ala Gln Ala Glu Lys Glu Lys Leu Leu Ala Glu
    210                 215                 220

Ile Ser Ser Asp Ile Asp Gln Leu Asn Pro Glu Ser Ala Asp Leu Arg
225                 230                 235                 240

Gln Ala Leu Ala Lys His Leu Tyr Asp Ser Tyr Ile Lys Ser Phe Pro
                245                 250                 255

Leu Thr Lys Ala Lys Ala Arg Ala Ile Leu Thr Gly Lys Thr Thr Asp
                260                 265                 270

Lys Ser Pro Phe Val Ile Tyr Asp Met Asn Ser Leu Met Met Gly Glu
            275                 280                 285

Asp Lys Ile Lys Phe Lys His Ile Thr Pro Leu Gln Glu Gln Ser Lys
        290                 295                 300

Glu Val Ala Ile Arg Ile Phe Gln Gly Cys Gln Phe Arg Ser Val Glu
305                 310                 315                 320

Ala Val Gln Glu Ile Thr Glu Tyr Ala Lys Ser Ile Pro Gly Phe Val
                325                 330                 335

Asn Leu Asp Leu Asn Asp Gln Val Thr Leu Leu Lys Tyr Gly Val His
                340                 345                 350

Glu Ile Ile Tyr Thr Met Leu Ala Ser Leu Met Asn Lys Asp Gly Val
            355                 360                 365

Leu Ile Ser Glu Gly Gln Gly Phe Met Thr Arg Glu Phe Leu Lys Ser
        370                 375                 380

Leu Arg Lys Pro Phe Gly Asp Phe Met Glu Pro Lys Phe Glu Phe Ala
385                 390                 395                 400

Val Lys Phe Asn Ala Leu Glu Leu Asp Asp Ser Asp Leu Ala Ile Phe
                405                 410                 415

Ile Ala Val Ile Ile Leu Ser Gly Asp Arg Pro Gly Leu Leu Asn Val
                420                 425                 430

Lys Pro Ile Glu Asp Ile Gln Asp Asn Leu Leu Gln Ala Leu Glu Leu
            435                 440                 445

Gln Leu Lys Leu Asn His Pro Glu Ser Ser Gln Leu Phe Ala Lys Leu
        450                 455                 460

Leu Gln Lys Met Thr Asp Leu Arg Gln Ile Val Thr Glu His Val Gln
465                 470                 475                 480

Leu Leu Gln Val Ile Lys Lys Thr Glu Thr Asp Met Ser Leu His Pro
                485                 490                 495

Leu Leu Gln Glu Ile Tyr Lys Asp Leu Tyr
            500                 505

<210> SEQ ID NO 7
<211> LENGTH: 7326
<212> TYPE: DNA
<213> ORGANISM: mouse
<220> FEATURE:
<221> NAME/KEY: CDS
<222> LOCATION: (1)..(7326)
<223> OTHER INFORMATION: n at position 1131 is unknown.

<400> SEQUENCE: 7 atg gcc gag aac ttg ctg gac gga ccg ccc aac ccc aaa cga gcc aaa    48
Met Ala Glu Asn Leu Leu Asp Gly Pro Pro Asn Pro Lys Arg Ala Lys
1               5                   10                  15 ctc agc tcg ccc ggc ttc tcc gcg aat gac aac aca gat ttt gga tca    96
Leu Ser Ser Pro Gly Phe Ser Ala Asn Asp Asn Thr Asp Phe Gly Ser
            20                  25                  30
```

-continued

| | |
|---|---|
| ttg ttt gac ttg gaa aat gac ctt cct gat gag ctg atc ccc aat gga<br>Leu Phe Asp Leu Glu Asn Asp Leu Pro Asp Glu Leu Ile Pro Asn Gly<br>35                    40                    45 | 144 |
| gaa tta agc ctt tta aac agt ggg aac ctt gtt cca gat gct gcg tcc<br>Glu Leu Ser Leu Leu Asn Ser Gly Asn Leu Val Pro Asp Ala Ala Ser<br>   50                    55                    60 | 192 |
| aaa cat aaa caa ctg tca gag ctt ctt aga gga ggc agc ggc tct agc<br>Lys His Lys Gln Leu Ser Glu Leu Leu Arg Gly Gly Ser Gly Ser Ser<br>65                    70                    75                    80 | 240 |
| atc aac cca ggg ata ggc aat gtg agt gcc agc agc cct gtg caa cag<br>Ile Asn Pro Gly Ile Gly Asn Val Ser Ala Ser Ser Pro Val Gln Gln<br>                  85                    90                    95 | 288 |
| ggc ctt ggt ggc cag gct cag ggg cag ccg aac agt aca aac atg gcc<br>Gly Leu Gly Gly Gln Ala Gln Gly Gln Pro Asn Ser Thr Asn Met Ala<br>                100                   105                 110 | 336 |
| agc tta ggt gcc atg ggc aag agc cct ctg aac caa gga gac tca tca<br>Ser Leu Gly Ala Met Gly Lys Ser Pro Leu Asn Gln Gly Asp Ser Ser<br>        115                    120                 125 | 384 |
| aca ccc aac ctg ccc aaa cag gca gcc agc acc tct ggg ccc act ccc<br>Thr Pro Asn Leu Pro Lys Gln Ala Ala Ser Thr Ser Gly Pro Thr Pro<br>130                    135                    140 | 432 |
| cct gcc tcc caa gca ctg aat cca caa gca caa aag caa gta ggg ctg<br>Pro Ala Ser Gln Ala Leu Asn Pro Gln Ala Gln Lys Gln Val Gly Leu<br>145                    150                    155                    160 | 480 |
| gtg acc agt agt cct gcc aca tca cag act gga cct ggg atc tgc atg<br>Val Thr Ser Ser Pro Ala Thr Ser Gln Thr Gly Pro Gly Ile Cys Met<br>                    165                    170                 175 | 528 |
| aat gct aac ttc aac cag acc cac cca ggc ctt ctc aat agt aac tct<br>Asn Ala Asn Phe Asn Gln Thr His Pro Gly Leu Leu Asn Ser Asn Ser<br>                180                    185                    190 | 576 |
| ggc cat agc tta atg aat cag gct caa caa ggg caa gct caa gtc atg<br>Gly His Ser Leu Met Asn Gln Ala Gln Gln Gly Gln Ala Gln Val Met<br>       195                    200                    205 | 624 |
| aat gga tct ctt ggg gct gct gga aga gga agg gga gct gga atg ccc<br>Asn Gly Ser Leu Gly Ala Ala Gly Arg Gly Arg Gly Ala Gly Met Pro<br>210                    215                    220 | 672 |
| tac cct gct cca gcc atg cag ggg gcc aca agc agt gtg ctg gcg gag<br>Tyr Pro Ala Pro Ala Met Gln Gly Ala Thr Ser Ser Val Leu Ala Glu<br>225                    230                    235                    240 | 720 |
| acc ttg aca cag gtt tcc cca caa atg gct ggc cat gct gga cta aat<br>Thr Leu Thr Gln Val Ser Pro Gln Met Ala Gly His Ala Gly Leu Asn<br>                    245                    250                 255 | 768 |
| aca gca cag gca gga ggc atg acc aag atg gga atg act ggt acc aca<br>Thr Ala Gln Ala Gly Gly Met Thr Lys Met Gly Met Thr Gly Thr Thr<br>                260                    265                 270 | 816 |
| agt cca ttt gga caa ccc ttt agt caa act gga ggg cag cag atg gga<br>Ser Pro Phe Gly Gln Pro Phe Ser Gln Thr Gly Gly Gln Gln Met Gly<br>       275                    280                 285 | 864 |
| gcc act gga gtg aac ccc cag tta gcc agc aaa cag agc atg gtc aat<br>Ala Thr Gly Val Asn Pro Gln Leu Ala Ser Lys Gln Ser Met Val Asn<br>290                    295                    300 | 912 |
| agt tta cct gct ttt cct aca gat atc aag aat act tca gtc acc act<br>Ser Leu Pro Ala Phe Pro Thr Asp Ile Lys Asn Thr Ser Val Thr Thr<br>305                    310                    315                    320 | 960 |
| gtg cca aat atg tcc cag ttg caa aca tca gtg gga att gta ccc aca<br>Val Pro Asn Met Ser Gln Leu Gln Thr Ser Val Gly Ile Val Pro Thr<br>                    325                    330                 335 | 1008 |
| caa gca att gca aca ggc ccc aca gca gac cct gaa aaa cgc aaa ctg<br>Gln Ala Ile Ala Thr Gly Pro Thr Ala Asp Pro Glu Lys Arg Lys Leu<br>                340                    345                 350 | 1056 |

-continued

| | |
|---|---|
| ata cag cag cag ctg gtt cta ctg ctt cat gcc cac aaa tgt cag aga<br>Ile Gln Gln Gln Leu Val Leu Leu Leu His Ala His Lys Cys Gln Arg<br>355                     360                    365 | 1104 |
| cga gag caa gca aat gga gag gtt cgn gcc tgt tct ctc cca cac tgt<br>Arg Glu Gln Ala Asn Gly Glu Val Arg Ala Cys Ser Leu Pro His Cys<br>    370                     375                    380 | 1152 |
| cga acc atg aaa aac gtt ttg aat cac atg aca cat tgt cag gct ccc<br>Arg Thr Met Lys Asn Val Leu Asn His Met Thr His Cys Gln Ala Pro<br>385                     390                    395                400 | 1200 |
| aaa gcc tgc caa gtt gcc cat tgt gca tct tca cga caa atc atc tct<br>Lys Ala Cys Gln Val Ala His Cys Ala Ser Ser Arg Gln Ile Ile Ser<br>                  405                    410                    415 | 1248 |
| cat tgg aag aac tgc aca cga cat gac tgt cct gtt tgc ctc cct ttg<br>His Trp Lys Asn Cys Thr Arg His Asp Cys Pro Val Cys Leu Pro Leu<br>                420                    425                    430 | 1296 |
| aaa aat gcc agt gac aag cga aac caa caa acc atc ctg gga tct cca<br>Lys Asn Ala Ser Asp Lys Arg Asn Gln Gln Thr Ile Leu Gly Ser Pro<br>                  435                    440                    445 | 1344 |
| gct agt gga att caa aac aca att ggt tct gtt ggt gca ggg caa cag<br>Ala Ser Gly Ile Gln Asn Thr Ile Gly Ser Val Gly Ala Gly Gln Gln<br>450                     455                    460 | 1392 |
| aat gcc act tcc tta agt aac cca aat ccc ata gac ccc agt tcc atg<br>Asn Ala Thr Ser Leu Ser Asn Pro Asn Pro Ile Asp Pro Ser Ser Met<br>465                     470                    475                    480 | 1440 |
| cag cgg gcc tat gct gct cta gga ctc ccc tac atg aac cag cct cag<br>Gln Arg Ala Tyr Ala Ala Leu Gly Leu Pro Tyr Met Asn Gln Pro Gln<br>                  485                    490                    495 | 1488 |
| acg cag ctg cag cct cag gtt cct ggc cag caa cca gca cag cct cca<br>Thr Gln Leu Gln Pro Gln Val Pro Gly Gln Gln Pro Ala Gln Pro Pro<br>    500                     505                    510 | 1536 |
| gcc cac cag cag atg agg act ctc aat gcc cta gga aac aac ccc atg<br>Ala His Gln Gln Met Arg Thr Leu Asn Ala Leu Gly Asn Asn Pro Met<br>515                     520                    525 | 1584 |
| agt gtc cca gca gga gga ata aca aca gat caa cag cca cca aac ttg<br>Ser Val Pro Ala Gly Gly Ile Thr Thr Asp Gln Gln Pro Pro Asn Leu<br>    530                     535                    540 | 1632 |
| att tca gaa tca gct ctt cca act tcc ttg ggg gct acc aat cca ctg<br>Ile Ser Glu Ser Ala Leu Pro Thr Ser Leu Gly Ala Thr Asn Pro Leu<br>545                     550                    555                    560 | 1680 |
| atg aat gat ggt tca aac tct ggt aac att gga agc ctc agc acg ata<br>Met Asn Asp Gly Ser Asn Ser Gly Asn Ile Gly Ser Leu Ser Thr Ile<br>                  565                    570                    575 | 1728 |
| cct aca gca gcg cct cct tcc agc act ggt gtt cga aaa ggc tgg cat<br>Pro Thr Ala Ala Pro Pro Ser Ser Thr Gly Val Arg Lys Gly Trp His<br>            580                    585                    590 | 1776 |
| gaa cat gtg act cag gac cta cgg agt cat cta gtc cat aaa ctc gtt<br>Glu His Val Thr Gln Asp Leu Arg Ser His Leu Val His Lys Leu Val<br>                  595                    600                    605 | 1824 |
| caa gcc atc ttc cca act cca gac cct gca gct ctg aaa gat cgc cgc<br>Gln Ala Ile Phe Pro Thr Pro Asp Pro Ala Ala Leu Lys Asp Arg Arg<br>610                     615                    620 | 1872 |
| atg gag aac ctg gtt gcc tat gct aag aaa gtg gag gga gac atg tat<br>Met Glu Asn Leu Val Ala Tyr Ala Lys Lys Val Glu Gly Asp Met Tyr<br>625                     630                    635                    640 | 1920 |
| gag tct gct aat agc agg gat gaa tac tat cat tta tta gca gag aaa<br>Glu Ser Ala Asn Ser Arg Asp Glu Tyr Tyr His Leu Leu Ala Glu Lys<br>                  645                    650                    655 | 1968 |
| atc tat aaa ata caa aaa gaa cta gaa gaa aag cgg agg aca cgt tta<br>Ile Tyr Lys Ile Gln Lys Glu Leu Glu Glu Lys Arg Arg Thr Arg Leu | 2016 |

```
                   660                 665                 670
cat aag caa ggc atc ctg ggt aac cag cca gct tta cca gct tct ggg      2064
His Lys Gln Gly Ile Leu Gly Asn Gln Pro Ala Leu Pro Ala Ser Gly
            675                 680                 685 gct cag ccc cct gtg att cca cca gcc cag tct gta aga cct cca aat      2112
Ala Gln Pro Pro Val Ile Pro Pro Ala Gln Ser Val Arg Pro Pro Asn
        690                 695                 700 ggg ccc ctg cct ttg cca gtg aat cgc atg cag gtt tct caa ggg atg      2160
Gly Pro Leu Pro Leu Pro Val Asn Arg Met Gln Val Ser Gln Gly Met
705                 710                 715                 720 aat tca ttt aac cca atg tcc ctg gga aac gtc cag ttg cca cag gca      2208
Asn Ser Phe Asn Pro Met Ser Leu Gly Asn Val Gln Leu Pro Gln Ala
                725                 730                 735 ccc atg gga cct cgt gca gcc tcc cct atg aac cac tct gtg cag atg      2256
Pro Met Gly Pro Arg Ala Ala Ser Pro Met Asn His Ser Val Gln Met
            740                 745                 750 aac agc atg gcc tca gtt ccg ggt atg gcc att tct cct tca cgg atg      2304
Asn Ser Met Ala Ser Val Pro Gly Met Ala Ile Ser Pro Ser Arg Met
        755                 760                 765 cct cag cct cca aat atg atg ggc act cat gcc aac aac att atg gcc      2352
Pro Gln Pro Pro Asn Met Met Gly Thr His Ala Asn Asn Ile Met Ala
770                 775                 780 cag gca cct act cag aac cag ttt ctg cca cag aac cag ttt cca tca      2400
Gln Ala Pro Thr Gln Asn Gln Phe Leu Pro Gln Asn Gln Phe Pro Ser
785                 790                 795                 800 tcc agt ggg gca atg agt gtg aac agt gtg ggc atg ggg caa cca gca      2448
Ser Ser Gly Ala Met Ser Val Asn Ser Val Gly Met Gly Gln Pro Ala
                805                 810                 815 gcc cag gca ggt gtt tca cag ggt cag gaa cct gga gct gct ctc cct      2496
Ala Gln Ala Gly Val Ser Gln Gly Gln Glu Pro Gly Ala Ala Leu Pro
            820                 825                 830 aac cct ctg aac atg ctg gca ccc cag gcc agc cag ctg cct tgc cca      2544
Asn Pro Leu Asn Met Leu Ala Pro Gln Ala Ser Gln Leu Pro Cys Pro
        835                 840                 845 cca gtg aca cag tca cca ttg cac ccg act cca cct cct gct tcc aca      2592
Pro Val Thr Gln Ser Pro Leu His Pro Thr Pro Pro Ala Ser Thr
850                 855                 860 gct gct ggc atg ccc tct ctc caa cat cca acg gca cca gga atg acc      2640
Ala Ala Gly Met Pro Ser Leu Gln His Pro Thr Ala Pro Gly Met Thr
865                 870                 875                 880 cct cct cag cca gca gct ccc act cag cca tct act cct gtg tca tct      2688
Pro Pro Gln Pro Ala Ala Pro Thr Gln Pro Ser Thr Pro Val Ser Ser
                885                 890                 895 ggg cag act cct acc cca act cct ggc tca gtg ccc agc gct gcc caa      2736
Gly Gln Thr Pro Thr Pro Thr Pro Gly Ser Val Pro Ser Ala Ala Gln
            900                 905                 910 aca cag agt acc cct aca gtc cag gca gca gca cag gct cag gtg act      2784
Thr Gln Ser Thr Pro Thr Val Gln Ala Ala Ala Gln Ala Gln Val Thr
        915                 920                 925 cca cag cct cag acc cca gtg cag cca cca tct gtg gct act cct cag      2832
Pro Gln Pro Gln Thr Pro Val Gln Pro Pro Ser Val Ala Thr Pro Gln
930                 935                 940 tca tca cag cag caa cca acg cct gtg cat act cag cca cct ggc aca      2880
Ser Ser Gln Gln Gln Pro Thr Pro Val His Thr Gln Pro Pro Gly Thr
945                 950                 955                 960 ccg ctt tct cag gca gca gcc agc att gat aat aga gtc cct act ccc      2928
Pro Leu Ser Gln Ala Ala Ala Ser Ile Asp Asn Arg Val Pro Thr Pro
                965                 970                 975 tcc act gtg acc agt gct gaa acc agt tcc cag cag cca gga ccc gat      2976
```

```
            Ser Thr Val Thr Ser Ala Glu Thr Ser Ser Gln Gln Pro Gly Pro Asp
                            980                 985                 990 gtg ccc atg ctg gaa atg aag aca gag gtg cag aca gat gat gct gag       3024
Val Pro Met Leu Glu Met Lys Thr Glu Val Gln Thr Asp Asp Ala Glu
            995                 1000                1005 cct gaa cct act gaa tcc aag ggg gaa cct cgg tct gag atg atg           3069
Pro Glu Pro Thr Glu Ser Lys Gly Glu Pro Arg Ser Glu Met Met
    1010                1015                1020 gaa gag gat tta caa ggt tct tcc caa gta aaa gaa gag aca gat           3114
Glu Glu Asp Leu Gln Gly Ser Ser Gln Val Lys Glu Glu Thr Asp
    1025                1030                1035 acg aca gag cag aag tca gag cca atg gaa gta gaa gaa aag aaa           3159
Thr Thr Glu Gln Lys Ser Glu Pro Met Glu Val Glu Glu Lys Lys
    1040                1045                1050 cct gaa gta aaa gtg gaa gct aaa gag gaa gaa gag aac agt tcg           3204
Pro Glu Val Lys Val Glu Ala Lys Glu Glu Glu Glu Asn Ser Ser
    1055                1060                1065 aac gac aca gcc tca caa tca aca tct cct tcc cag cca cgc aaa           3249
Asn Asp Thr Ala Ser Gln Ser Thr Ser Pro Ser Gln Pro Arg Lys
    1070                1075                1080 aaa atc ttt aaa ccc gag gag cta cgc cag gca ctt atg cca act           3294
Lys Ile Phe Lys Pro Glu Glu Leu Arg Gln Ala Leu Met Pro Thr
    1085                1090                1095 cta gaa gca ctc tat cga cag gac cca gag tct ttg cct ttt cgt           3339
Leu Glu Ala Leu Tyr Arg Gln Asp Pro Glu Ser Leu Pro Phe Arg
    1100                1105                1110 cag cct gta gat cct cag ctc cta gga atc cca gat tat ttt gat           3384
Gln Pro Val Asp Pro Gln Leu Leu Gly Ile Pro Asp Tyr Phe Asp
    1115                1120                1125 ata gtg aag aat cct atg gac ctt tct acc atc aaa cga aag ctg           3429
Ile Val Lys Asn Pro Met Asp Leu Ser Thr Ile Lys Arg Lys Leu
    1130                1135                1140 gac aca ggg caa tat caa gaa ccc tgg cag tat gtg gat gat gtc           3474
Asp Thr Gly Gln Tyr Gln Glu Pro Trp Gln Tyr Val Asp Asp Val
    1145                1150                1155 agg ctt atg ttc aac aat gcg tgg cta tat aat cgt aaa acg tcc           3519
Arg Leu Met Phe Asn Asn Ala Trp Leu Tyr Asn Arg Lys Thr Ser
    1160                1165                1170 cgt gta tat aaa ttt tgc agt aaa ctt gca gag gtc ttt gaa caa           3564
Arg Val Tyr Lys Phe Cys Ser Lys Leu Ala Glu Val Phe Glu Gln
    1175                1180                1185 gaa att gac cct gtc atg cag tct ctt gga tat tgc tgt gga cga           3609
Glu Ile Asp Pro Val Met Gln Ser Leu Gly Tyr Cys Cys Gly Arg
    1190                1195                1200 aag tat gag ttc tcc cca cag act ttg tgc tgt tac gga aag cag           3654
Lys Tyr Glu Phe Ser Pro Gln Thr Leu Cys Cys Tyr Gly Lys Gln
    1205                1210                1215 ctg tgt aca att cct cgt gat gca gcc tac tac agc tat cag aat           3699
Leu Cys Thr Ile Pro Arg Asp Ala Ala Tyr Tyr Ser Tyr Gln Asn
    1220                1225                1230 agg tat cat ttc tgt ggg aag tgt ttc aca gag atc cag ggc gag           3744
Arg Tyr His Phe Cys Gly Lys Cys Phe Thr Glu Ile Gln Gly Glu
    1235                1240                1245 aat gtg acc ctg ggt gac gac cct tcc caa cct cag acg aca att           3789
Asn Val Thr Leu Gly Asp Asp Pro Ser Gln Pro Gln Thr Thr Ile
    1250                1255                1260 tcc aag gat caa ttt gaa aag aag aaa aat gat acc tta gat cct           3834
Ser Lys Asp Gln Phe Glu Lys Lys Lys Asn Asp Thr Leu Asp Pro
    1265                1270                1275
```

| | | | | | | | | | | | | |
|---|---|---|---|---|---|---|---|---|---|---|---|---|
| gaa | cct | ttt | gtt | gac | tgc | aaa | gag | tgt | ggc | cgg | aag | atg cat cag | 3879 |
| Glu | Pro | Phe | Val | Asp | Cys | Lys | Glu | Cys | Gly | Arg | Lys | Met His Gln | |
| | 1280 | | | | 1285 | | | | 1290 | | | | |
| att | tgt | gtt | cta | cac | tat | gac | atc | att | tgg | cct | tca | ggt ttt gtg | 3924 |
| Ile | Cys | Val | Leu | His | Tyr | Asp | Ile | Ile | Trp | Pro | Ser | Gly Phe Val | |
| | 1295 | | | | 1300 | | | | 1305 | | | | |
| tgt | gac | aac | tgt | ttg | aag | aaa | act | ggc | aga | cct | cgg | aaa gaa aac | 3969 |
| Cys | Asp | Asn | Cys | Leu | Lys | Lys | Thr | Gly | Arg | Pro | Arg | Lys Glu Asn | |
| 1310 | | | | | 1315 | | | | 1320 | | | | |
| aaa | ttc | agt | gct | aag | agg | ctg | cag | acc | aca | cga | ttg | gga aac cac | 4014 |
| Lys | Phe | Ser | Ala | Lys | Arg | Leu | Gln | Thr | Thr | Arg | Leu | Gly Asn His | |
| 1325 | | | | | 1330 | | | | 1335 | | | | |
| tta | gaa | gac | aga | gtg | aat | aag | ttt | ttg | cgg | cgc | cag | aat cac cct | 4059 |
| Leu | Glu | Asp | Arg | Val | Asn | Lys | Phe | Leu | Arg | Arg | Gln | Asn His Pro | |
| 1340 | | | | | 1345 | | | | 1350 | | | | |
| gaa | gct | ggg | gag | gtt | ttt | gtc | aga | gtg | gtg | gcc | agc | tca gac aag | 4104 |
| Glu | Ala | Gly | Glu | Val | Phe | Val | Arg | Val | Val | Ala | Ser | Ser Asp Lys | |
| 1355 | | | | | 1360 | | | | 1365 | | | | |
| act | gtg | gag | gtc | aag | ccg | gga | atg | aag | tca | agg | ttt | gtg gat tct | 4149 |
| Thr | Val | Glu | Val | Lys | Pro | Gly | Met | Lys | Ser | Arg | Phe | Val Asp Ser | |
| 1370 | | | | | 1375 | | | | 1380 | | | | |
| gga | gag | atg | tcg | gaa | tct | ttc | cca | tat | cgt | acc | aaa | gca ctc ttt | 4194 |
| Gly | Glu | Met | Ser | Glu | Ser | Phe | Pro | Tyr | Arg | Thr | Lys | Ala Leu Phe | |
| 1385 | | | | | 1390 | | | | 1395 | | | | |
| gct | ttt | gag | gag | atc | gat | gga | gtc | gat | gtg | tgc | ttt | ttt ggg atg | 4239 |
| Ala | Phe | Glu | Glu | Ile | Asp | Gly | Val | Asp | Val | Cys | Phe | Phe Gly Met | |
| 1400 | | | | | 1405 | | | | 1410 | | | | |
| cat | gtg | caa | gat | acg | gct | ctg | att | gcc | ccc | cac | caa | ata caa ggc | 4284 |
| His | Val | Gln | Asp | Thr | Ala | Leu | Ile | Ala | Pro | His | Gln | Ile Gln Gly | |
| 1415 | | | | | 1420 | | | | 1425 | | | | |
| tgt | gta | tac | ata | tct | tat | ctg | gac | agt | att | cat | ttc | ttc cgg ccc | 4329 |
| Cys | Val | Tyr | Ile | Ser | Tyr | Leu | Asp | Ser | Ile | His | Phe | Phe Arg Pro | |
| 1430 | | | | | 1435 | | | | 1440 | | | | |
| cgc | tgc | ctc | cgg | aca | gct | gtt | tac | cat | gag | atc | ctc | atc gga tat | 4374 |
| Arg | Cys | Leu | Arg | Thr | Ala | Val | Tyr | His | Glu | Ile | Leu | Ile Gly Tyr | |
| 1445 | | | | | 1450 | | | | 1455 | | | | |
| ctc | gag | tat | gtg | aag | aaa | ttg | gtg | tat | gtg | aca | gca | cat att tgg | 4419 |
| Leu | Glu | Tyr | Val | Lys | Lys | Leu | Val | Tyr | Val | Thr | Ala | His Ile Trp | |
| 1460 | | | | | 1465 | | | | 1470 | | | | |
| gcc | tgt | ccc | cca | agt | gaa | gga | gat | gac | tat | atc | ttt | cat tgc cac | 4464 |
| Ala | Cys | Pro | Pro | Ser | Glu | Gly | Asp | Asp | Tyr | Ile | Phe | His Cys His | |
| 1475 | | | | | 1480 | | | | 1485 | | | | |
| ccc | cct | gac | cag | aaa | atc | ccc | aaa | cca | aaa | cga | cta | cag gag tgg | 4509 |
| Pro | Pro | Asp | Gln | Lys | Ile | Pro | Lys | Pro | Lys | Arg | Leu | Gln Glu Trp | |
| 1490 | | | | | 1495 | | | | 1500 | | | | |
| tac | aag | aag | atg | ctg | gac | aag | gcg | ttt | gca | gag | agg | atc att aac | 4554 |
| Tyr | Lys | Lys | Met | Leu | Asp | Lys | Ala | Phe | Ala | Glu | Arg | Ile Ile Asn | |
| 1505 | | | | | 1510 | | | | 1515 | | | | |
| gac | tat | aag | gac | atc | ttc | aaa | caa | gcg | aac | gaa | gac | agg ctc acg | 4599 |
| Asp | Tyr | Lys | Asp | Ile | Phe | Lys | Gln | Ala | Asn | Glu | Asp | Arg Leu Thr | |
| 1520 | | | | | 1525 | | | | 1530 | | | | |
| agt | gcc | aag | gag | ttg | ccc | tat | ttt | gaa | gga | gat | ttc | tgg cct aat | 4644 |
| Ser | Ala | Lys | Glu | Leu | Pro | Tyr | Phe | Glu | Gly | Asp | Phe | Trp Pro Asn | |
| 1535 | | | | | 1540 | | | | 1545 | | | | |
| gtg | ttg | gaa | gaa | agc | att | aag | gaa | cta | gaa | caa | gaa | gaa gaa gaa | 4689 |
| Val | Leu | Glu | Glu | Ser | Ile | Lys | Glu | Leu | Glu | Gln | Glu | Glu Glu Glu | |
| 1550 | | | | | 1555 | | | | 1560 | | | | |
| agg | aaa | aaa | gaa | gag | agt | act | gca | gcg | agt | gag | act | cct gag ggc | 4734 |
| Arg | Lys | Lys | Glu | Glu | Ser | Thr | Ala | Ala | Ser | Glu | Thr | Pro Glu Gly | |
| 1565 | | | | | 1570 | | | | 1575 | | | | |

-continued

| | | | | | | | | | | | | | | |
|---|---|---|---|---|---|---|---|---|---|---|---|---|---|---|
| agt | cag | ggt | gac | agc | aaa | aat | gcg | aag | aaa | aag | aac | aac | aag | aag | 4779 |
| Ser | Gln | Gly | Asp | Ser | Lys | Asn | Ala | Lys | Lys | Lys | Asn | Asn | Lys | Lys | |
| | 1580 | | | | 1585 | | | | 1590 | | | | | | |
| acc | aac | aaa | aac | aaa | agc | agc | att | agc | cgc | gcc | aac | aag | aag | aag | 4824 |
| Thr | Asn | Lys | Asn | Lys | Ser | Ser | Ile | Ser | Arg | Ala | Asn | Lys | Lys | Lys | |
| 1595 | | | | | 1600 | | | | | 1605 | | | | | |
| ccc | agc | atg | ccc | aat | gtt | tcc | aac | gac | ctg | tcg | cag | aag | ctg | tat | 4869 |
| Pro | Ser | Met | Pro | Asn | Val | Ser | Asn | Asp | Leu | Ser | Gln | Lys | Leu | Tyr | |
| 1610 | | | | | 1615 | | | | | 1620 | | | | | |
| gcc | acc | atg | gag | aag | cac | aag | gag | gta | ttc | ttt | gtg | att | cat | ctg | 4914 |
| Ala | Thr | Met | Glu | Lys | His | Lys | Glu | Val | Phe | Phe | Val | Ile | His | Leu | |
| 1625 | | | | | 1630 | | | | | 1635 | | | | | |
| cat | gct | ggg | cct | gtt | atc | agc | act | cag | ccc | ccc | atc | gtg | gac | cct | 4959 |
| His | Ala | Gly | Pro | Val | Ile | Ser | Thr | Gln | Pro | Pro | Ile | Val | Asp | Pro | |
| 1640 | | | | | 1645 | | | | | 1650 | | | | | |
| gat | cct | ctg | ctt | agc | tgt | gac | ctc | atg | gat | ggg | cga | gat | gcc | ttc | 5004 |
| Asp | Pro | Leu | Leu | Ser | Cys | Asp | Leu | Met | Asp | Gly | Arg | Asp | Ala | Phe | |
| 1655 | | | | | 1660 | | | | | 1665 | | | | | |
| ctc | acc | ctg | gcc | aga | gac | aag | cac | tgg | gaa | ttc | tct | tcc | tta | cgc | 5049 |
| Leu | Thr | Leu | Ala | Arg | Asp | Lys | His | Trp | Glu | Phe | Ser | Ser | Leu | Arg | |
| 1670 | | | | | 1675 | | | | | 1680 | | | | | |
| cgc | tcc | aaa | tgg | tcc | act | ctg | tgc | atg | ctg | gtg | gag | ctg | cac | aca | 5094 |
| Arg | Ser | Lys | Trp | Ser | Thr | Leu | Cys | Met | Leu | Val | Glu | Leu | His | Thr | |
| 1685 | | | | | 1690 | | | | | 1695 | | | | | |
| cag | ggc | cag | gac | cgc | ttt | gtt | tat | acc | tgc | aat | gag | tgc | aaa | cac | 5139 |
| Gln | Gly | Gln | Asp | Arg | Phe | Val | Tyr | Thr | Cys | Asn | Glu | Cys | Lys | His | |
| 1700 | | | | | 1705 | | | | | 1710 | | | | | |
| cat | gtg | gaa | aca | cgc | tgg | cac | tgc | act | gtg | tgt | gag | gac | tat | gac | 5184 |
| His | Val | Glu | Thr | Arg | Trp | His | Cys | Thr | Val | Cys | Glu | Asp | Tyr | Asp | |
| 1715 | | | | | 1720 | | | | | 1725 | | | | | |
| ctt | tgt | atc | aat | tgc | tac | aac | aca | aag | agc | cac | acc | cat | aag | atg | 5229 |
| Leu | Cys | Ile | Asn | Cys | Tyr | Asn | Thr | Lys | Ser | His | Thr | His | Lys | Met | |
| 1730 | | | | | 1735 | | | | | 1740 | | | | | |
| gtg | aag | tgg | ggg | cta | ggc | cta | gat | gat | gag | ggc | agc | agt | cag | ggt | 5274 |
| Val | Lys | Trp | Gly | Leu | Gly | Leu | Asp | Asp | Glu | Gly | Ser | Ser | Gln | Gly | |
| 1745 | | | | | 1750 | | | | | 1755 | | | | | |
| gag | cca | cag | tcc | aag | agc | ccc | cag | gaa | tcc | cgg | cgt | ctc | agc | atc | 5319 |
| Glu | Pro | Gln | Ser | Lys | Ser | Pro | Gln | Glu | Ser | Arg | Arg | Leu | Ser | Ile | |
| 1760 | | | | | 1765 | | | | | 1770 | | | | | |
| cag | cgc | tgc | atc | cag | tcc | ctg | gtg | cat | gcc | tgc | cag | tgt | cgc | aat | 5364 |
| Gln | Arg | Cys | Ile | Gln | Ser | Leu | Val | His | Ala | Cys | Gln | Cys | Arg | Asn | |
| 1775 | | | | | 1780 | | | | | 1785 | | | | | |
| gcc | aac | tgc | tca | ctg | ccg | tct | tgc | cag | aag | atg | aag | cga | gtc | gtg | 5409 |
| Ala | Asn | Cys | Ser | Leu | Pro | Ser | Cys | Gln | Lys | Met | Lys | Arg | Val | Val | |
| 1790 | | | | | 1795 | | | | | 1800 | | | | | |
| cag | cac | acc | aag | ggc | tgc | aag | cgc | aag | act | aat | gga | gga | tgc | cca | 5454 |
| Gln | His | Thr | Lys | Gly | Cys | Lys | Arg | Lys | Thr | Asn | Gly | Gly | Cys | Pro | |
| 1805 | | | | | 1810 | | | | | 1815 | | | | | |
| gtg | tgc | aag | cag | ctc | att | gct | ctt | tgc | tgc | tac | cac | gcc | aaa | cac | 5499 |
| Val | Cys | Lys | Gln | Leu | Ile | Ala | Leu | Cys | Cys | Tyr | His | Ala | Lys | His | |
| 1820 | | | | | 1825 | | | | | 1830 | | | | | |
| tgc | caa | gaa | aat | aaa | tgc | cct | gtg | ccc | ttc | tgc | ctc | aac | atc | aaa | 5544 |
| Cys | Gln | Glu | Asn | Lys | Cys | Pro | Val | Pro | Phe | Cys | Leu | Asn | Ile | Lys | |
| 1835 | | | | | 1840 | | | | | 1845 | | | | | |
| cat | aac | gtc | cgc | cag | cag | cag | atc | cag | cac | tgc | ctg | cag | cag | gct | 5589 |
| His | Asn | Val | Arg | Gln | Gln | Gln | Ile | Gln | His | Cys | Leu | Gln | Gln | Ala | |
| 1850 | | | | | 1855 | | | | | 1860 | | | | | |
| cag | ctc | atg | cgc | cgg | cga | atg | gca | acc | atg | aac | acc | cgc | aat | gtg | 5634 |
| Gln | Leu | Met | Arg | Arg | Arg | Met | Ala | Thr | Met | Asn | Thr | Arg | Asn | Val | |

-continued

|  |  |  |  | 1865 |  |  |  | 1870 |  |  |  | 1875 |  |  |  |
|---|---|---|---|---|---|---|---|---|---|---|---|---|---|---|---|
| cct<br>Pro | cag<br>Gln | cag<br>Gln | agt<br>Ser | ttg<br>Leu<br>1880 | cct<br>Pro | tct<br>Ser | cct<br>Pro | acc<br>Thr<br>1885 | tca<br>Ser | gca<br>Ala | cca<br>Pro | ccc<br>Pro<br>1890 | ggg<br>Gly | act<br>Thr | 5679 |
| cct<br>Pro | aca<br>Thr<br>1895 | cag<br>Gln | cag<br>Gln | ccc<br>Pro | agc<br>Ser | aca<br>Thr<br>1900 | ccc<br>Pro | caa<br>Gln | aca<br>Thr | cca<br>Pro | cag<br>Gln<br>1905 | ccc<br>Pro | cca<br>Pro | gcc<br>Ala | 5724 |
| cag<br>Gln | cct<br>Pro<br>1910 | cag<br>Gln | cct<br>Pro | tca<br>Ser | cct<br>Pro | gtt<br>Val<br>1915 | aac<br>Asn | atg<br>Met | tca<br>Ser | cca<br>Pro | gca<br>Ala<br>1920 | ggc<br>Gly | ttc<br>Phe | cct<br>Pro | 5769 |
| aat<br>Asn | gta<br>Val<br>1925 | gcc<br>Ala | cgg<br>Arg | act<br>Thr | cag<br>Gln | ccc<br>Pro<br>1930 | cca<br>Pro | aca<br>Thr | ata<br>Ile | gtg<br>Val | tct<br>Ser<br>1935 | gct<br>Ala | ggg<br>Gly | aag<br>Lys | 5814 |
| cct<br>Pro | acc<br>Thr<br>1940 | aac<br>Asn | cag<br>Gln | gtg<br>Val | cca<br>Pro | gct<br>Ala<br>1945 | ccc<br>Pro | cca<br>Pro | ccc<br>Pro | cct<br>Pro | gcc<br>Ala<br>1950 | cag<br>Gln | ccc<br>Pro | cca<br>Pro | 5859 |
| cct<br>Pro | gca<br>Ala<br>1955 | gca<br>Ala | gta<br>Val | gaa<br>Glu | gca<br>Ala | gcc<br>Ala<br>1960 | cgg<br>Arg | caa<br>Gln | att<br>Ile | gaa<br>Glu | cgt<br>Arg<br>1965 | gag<br>Glu | gcc<br>Ala | cag<br>Gln | 5904 |
| cag<br>Gln | cag<br>Gln<br>1970 | cag<br>Gln | cac<br>His | cta<br>Leu | tac<br>Tyr | cga<br>Arg<br>1975 | gca<br>Ala | aac<br>Asn | atc<br>Ile | aac<br>Asn | aat<br>Asn<br>1980 | ggc<br>Gly | atg<br>Met | ccc<br>Pro | 5949 |
| cca<br>Pro | gga<br>Gly<br>1985 | cgt<br>Arg | gac<br>Asp | ggt<br>Gly | atg<br>Met | ggg<br>Gly<br>1990 | acc<br>Thr | cca<br>Pro | gga<br>Gly | agc<br>Ser | caa<br>Gln<br>1995 | atg<br>Met | act<br>Thr | cct<br>Pro | 5994 |
| gtg<br>Val | ggc<br>Gly<br>2000 | ctg<br>Leu | aat<br>Asn | gtg<br>Val | ccc<br>Pro | cgt<br>Arg<br>2005 | ccc<br>Pro | aac<br>Asn | caa<br>Gln | gtc<br>Val | agt<br>Ser<br>2010 | ggg<br>Gly | cct<br>Pro | gtc<br>Val | 6039 |
| atg<br>Met | tct<br>Ser<br>2015 | agt<br>Ser | atg<br>Met | cca<br>Pro | cct<br>Pro | ggg<br>Gly<br>2020 | cag<br>Gln | tgg<br>Trp | cag<br>Gln | cag<br>Gln | gca<br>Ala<br>2025 | ccc<br>Pro | atc<br>Ile | cct<br>Pro | 6084 |
| cag<br>Gln | cag<br>Gln<br>2030 | cag<br>Gln | ccg<br>Pro | atg<br>Met | cca<br>Pro | ggc<br>Gly<br>2035 | atg<br>Met | ccc<br>Pro | agg<br>Arg | cct<br>Pro | gta<br>Val<br>2040 | atg<br>Met | tcc<br>Ser | atg<br>Met | 6129 |
| cag<br>Gln | gcc<br>Ala<br>2045 | cag<br>Gln | gca<br>Ala | gca<br>Ala | gtg<br>Val | gct<br>Ala<br>2050 | ggg<br>Gly | cca<br>Pro | cgg<br>Arg | atg<br>Met | ccc<br>Pro<br>2055 | aat<br>Asn | gtg<br>Val | cag<br>Gln | 6174 |
| cca<br>Pro | aac<br>Asn<br>2060 | agg<br>Arg | agc<br>Ser | atc<br>Ile | tcg<br>Ser | cca<br>Pro<br>2065 | agt<br>Ser | gcc<br>Ala | ctg<br>Leu | caa<br>Gln | gac<br>Asp<br>2070 | ctg<br>Leu | cta<br>Leu | cgg<br>Arg | 6219 |
| acc<br>Thr | cta<br>Leu<br>2075 | aag<br>Lys | tca<br>Ser | ccc<br>Pro | agc<br>Ser | tct<br>Ser<br>2080 | cct<br>Pro | cag<br>Gln | cag<br>Gln | cag<br>Gln | cag<br>Gln<br>2085 | gtg<br>Val | ctg<br>Leu |  | 6264 |
| aac<br>Asn | atc<br>Ile<br>2090 | ctt<br>Leu | aaa<br>Lys | tca<br>Ser | aac<br>Asn | cca<br>Pro<br>2095 | cag<br>Gln | cta<br>Leu | atg<br>Met | gca<br>Ala | gct<br>Ala<br>2100 | ttc<br>Phe | atc<br>Ile | aaa<br>Lys | 6309 |
| cag<br>Gln | cgc<br>Arg<br>2105 | aca<br>Thr | gcc<br>Ala | aag<br>Lys | tat<br>Tyr | gtg<br>Val<br>2110 | gcc<br>Ala | aat<br>Asn | cag<br>Gln | cct<br>Pro | ggc<br>Gly<br>2115 | atg<br>Met | cag<br>Gln | ccc<br>Pro | 6354 |
| cag<br>Gln | ccc<br>Pro<br>2120 | gga<br>Gly | ctt<br>Leu | caa<br>Gln | tcc<br>Ser | cag<br>Gln<br>2125 | cct<br>Pro | ggt<br>Gly | atg<br>Met | cag<br>Gln | ccc<br>Pro<br>2130 | cag<br>Gln | cct<br>Pro | ggc<br>Gly | 6399 |
| atg<br>Met | cac<br>His<br>2135 | cag<br>Gln | cag<br>Gln | cct<br>Pro | agt<br>Ser | ttg<br>Leu<br>2140 | caa<br>Gln | aac<br>Asn | ctg<br>Leu | aac<br>Asn | gca<br>Ala<br>2145 | atg<br>Met | caa<br>Gln | gct<br>Ala | 6444 |
| ggt<br>Gly | gtg<br>Val<br>2150 | cca<br>Pro | cgg<br>Arg | cct<br>Pro | ggt<br>Gly | gtg<br>Val<br>2155 | cct<br>Pro | cca<br>Pro | cca<br>Pro | caa<br>Gln | cca<br>Pro<br>2160 | gca<br>Ala | atg<br>Met | gga<br>Gly | 6489 |
| ggc<br>Gly | ctg<br>Leu | aat<br>Asn | ccc<br>Pro | cag<br>Gln | gga<br>Gly | caa<br>Gln | gct<br>Ala | ctg<br>Leu | aac<br>Asn | atc<br>Ile | atg<br>Met | aac<br>Asn | cca<br>Pro | gga<br>Gly | 6534 |

-continued

| | | | | | | | | | | |
|---|---|---|---|---|---|---|---|---|---|---|
| Gly | Leu | Asn | Pro | Gln | Gly | Gln | Ala | Leu | Asn | Ile | Met | Asn | Pro | Gly |
| | 2165 | | | | 2170 | | | | 2175 | |

```
cac aac ccc aac atg aca aac atg aat cca cag tac cga gaa atg      6579
His Asn Pro Asn Met Thr Asn Met Asn Pro Gln Tyr Arg Glu Met
    2180            2185            2190 gtg agg aga cag ctg cta cag cac cag cag cag cag caa cag          6624
Val Arg Arg Gln Leu Leu Gln His Gln Gln Gln Gln Gln Gln
    2195            2200            2205 cag cag cag cag cag caa caa caa aat agt gcc agc ttg gcc ggg      6669
Gln Gln Gln Gln Gln Gln Gln Asn Ser Ala Ser Leu Ala Gly
    2210            2215            2220 ggc atg gcg gga cac agc cag ttc cag cag cca caa gga cct gga      6714
Gly Met Ala Gly His Ser Gln Phe Gln Gln Pro Gln Gly Pro Gly
    2225            2230            2235 ggt tat gcc cca gcc atg cag cag caa cgc atg caa cag cac ctc      6759
Gly Tyr Ala Pro Ala Met Gln Gln Gln Arg Met Gln Gln His Leu
    2240            2245            2250 ccc atc cag ggc agc tcc atg ggc cag atg gct gct cca atg gga      6804
Pro Ile Gln Gly Ser Ser Met Gly Gln Met Ala Ala Pro Met Gly
    2255            2260            2265 caa ctt ggc cag atg ggg cag cct ggg cta ggg gca gac agc acc      6849
Gln Leu Gly Gln Met Gly Gln Pro Gly Leu Gly Ala Asp Ser Thr
    2270            2275            2280 cct aat atc cag cag gcc ctg cag caa cgg att ctg cag cag cag      6894
Pro Asn Ile Gln Gln Ala Leu Gln Gln Arg Ile Leu Gln Gln Gln
    2285            2290            2295 cag atg aag caa caa att ggg tca cca ggc cag ccg aac ccc atg      6939
Gln Met Lys Gln Gln Ile Gly Ser Pro Gly Gln Pro Asn Pro Met
    2300            2305            2310 agc ccc cag cag cac atg ctc tca gga cag cca cag gcc tca cat      6984
Ser Pro Gln Gln His Met Leu Ser Gly Gln Pro Gln Ala Ser His
    2315            2320            2325 ctc cct ggc cag cag atc gcc aca tcc ctt agt aac cag gtg cga      7029
Leu Pro Gly Gln Gln Ile Ala Thr Ser Leu Ser Asn Gln Val Arg
    2330            2335            2340 tct cca gcc cct gtg cag tct cca cgg ccc caa tcc caa cct cca      7074
Ser Pro Ala Pro Val Gln Ser Pro Arg Pro Gln Ser Gln Pro Pro
    2345            2350            2355 cat tcc agc ccg tca cca cgg ata caa ccc cag cct tca cca cac      7119
His Ser Ser Pro Ser Pro Arg Ile Gln Pro Gln Pro Ser Pro His
    2360            2365            2370 cat gtt tca ccc cag act gga acc cct cac cct gga ctc gca gtc      7164
His Val Ser Pro Gln Thr Gly Thr Pro His Pro Gly Leu Ala Val
    2375            2380            2385 acc atg gcc agc tcc atg gat cag gga cac ctg ggg aac cct gaa      7209
Thr Met Ala Ser Ser Met Asp Gln Gly His Leu Gly Asn Pro Glu
    2390            2395            2400 cag agt gca atg ctc ccc cag ctg aat acc ccc aac agg agc gca      7254
Gln Ser Ala Met Leu Pro Gln Leu Asn Thr Pro Asn Arg Ser Ala
    2405            2410            2415 ctg tcc agt gaa ctg tcc ctg gtt ggt gat acc acg gga gac aca      7299
Leu Ser Ser Glu Leu Ser Leu Val Gly Asp Thr Thr Gly Asp Thr
    2420            2425            2430 cta gaa aag ttt gtg gag ggt ttg tag                              7326
Leu Glu Lys Phe Val Glu Gly Leu
    2435            2440
```

<210> SEQ ID NO 8
<211> LENGTH: 2441
<212> TYPE: PRT

<213> ORGANISM: mouse

<400> SEQUENCE: 8

| | | | | | | | | | | | | | | |
|---|---|---|---|---|---|---|---|---|---|---|---|---|---|---|
|Met|Ala|Glu|Asn|Leu|Leu|Asp|Gly|Pro|Pro|Asn|Pro|Lys|Arg|Ala|Lys|
|1| | | |5| | | | |10| | | | |15| |

Leu Ser Ser Pro Gly Phe Ser Ala Asn Asp Asn Thr Asp Phe Gly Ser
                20                  25                  30

Leu Phe Asp Leu Glu Asn Asp Leu Pro Asp Glu Leu Ile Pro Asn Gly
            35                  40                  45

Glu Leu Ser Leu Leu Asn Ser Gly Asn Leu Val Pro Asp Ala Ala Ser
50                  55                  60

Lys His Lys Gln Leu Ser Glu Leu Leu Arg Gly Gly Ser Gly Ser Ser
65                  70                  75                  80

Ile Asn Pro Gly Ile Gly Asn Val Ser Ala Ser Ser Pro Val Gln Gln
                85                  90                  95

Gly Leu Gly Gly Gln Ala Gln Gly Gln Pro Asn Ser Thr Asn Met Ala
                100                 105                 110

Ser Leu Gly Ala Met Gly Lys Ser Pro Leu Asn Gln Gly Asp Ser Ser
            115                 120                 125

Thr Pro Asn Leu Pro Lys Gln Ala Ala Ser Thr Ser Gly Pro Thr Pro
130                 135                 140

Pro Ala Ser Gln Ala Leu Asn Pro Gln Ala Gln Lys Gln Val Gly Leu
145                 150                 155                 160

Val Thr Ser Ser Pro Ala Thr Ser Gln Thr Gly Pro Gly Ile Cys Met
                165                 170                 175

Asn Ala Asn Phe Asn Gln Thr His Pro Gly Leu Leu Asn Ser Asn Ser
            180                 185                 190

Gly His Ser Leu Met Asn Gln Ala Gln Gln Gly Gln Ala Gln Val Met
            195                 200                 205

Asn Gly Ser Leu Gly Ala Ala Gly Arg Gly Arg Gly Ala Gly Met Pro
210                 215                 220

Tyr Pro Ala Pro Ala Met Gln Gly Ala Thr Ser Ser Val Leu Ala Glu
225                 230                 235                 240

Thr Leu Thr Gln Val Ser Pro Gln Met Ala Gly His Ala Gly Leu Asn
                245                 250                 255

Thr Ala Gln Ala Gly Gly Met Thr Lys Met Gly Met Thr Gly Thr Thr
            260                 265                 270

Ser Pro Phe Gly Gln Pro Phe Ser Gln Thr Gly Gly Gln Gln Met Gly
            275                 280                 285

Ala Thr Gly Val Asn Pro Gln Leu Ala Ser Lys Gln Ser Met Val Asn
290                 295                 300

Ser Leu Pro Ala Phe Pro Thr Asp Ile Lys Asn Thr Ser Val Thr Thr
305                 310                 315                 320

Val Pro Asn Met Ser Gln Leu Gln Thr Ser Val Gly Ile Val Pro Thr
                325                 330                 335

Gln Ala Ile Ala Thr Gly Pro Thr Ala Asp Pro Glu Lys Arg Lys Leu
            340                 345                 350

Ile Gln Gln Gln Leu Val Leu Leu Leu His Ala His Lys Cys Gln Arg
            355                 360                 365

Arg Glu Gln Ala Asn Gly Glu Val Arg Ala Cys Ser Leu Pro His Cys
            370                 375                 380

Arg Thr Met Lys Asn Val Leu Asn His Met Thr His Cys Gln Ala Pro
385                 390                 395                 400

-continued

```
Lys Ala Cys Gln Val Ala His Cys Ala Ser Ser Arg Gln Ile Ile Ser
            405                 410                 415
His Trp Lys Asn Cys Thr Arg His Asp Cys Pro Val Cys Leu Pro Leu
            420                 425                 430
Lys Asn Ala Ser Asp Lys Arg Asn Gln Gln Thr Ile Leu Gly Ser Pro
            435                 440                 445
Ala Ser Gly Ile Gln Asn Thr Ile Gly Ser Val Gly Ala Gly Gln Gln
        450                 455                 460
Asn Ala Thr Ser Leu Ser Asn Pro Asn Pro Ile Asp Pro Ser Ser Met
465                 470                 475                 480
Gln Arg Ala Tyr Ala Ala Leu Gly Leu Pro Tyr Met Asn Gln Pro Gln
                485                 490                 495
Thr Gln Leu Gln Pro Gln Val Pro Gly Gln Gln Pro Ala Gln Pro Pro
            500                 505                 510
Ala His Gln Gln Met Arg Thr Leu Asn Ala Leu Gly Asn Asn Pro Met
        515                 520                 525
Ser Val Pro Ala Gly Gly Ile Thr Thr Asp Gln Gln Pro Pro Asn Leu
    530                 535                 540
Ile Ser Glu Ser Ala Leu Pro Thr Ser Leu Gly Ala Thr Asn Pro Leu
545                 550                 555                 560
Met Asn Asp Gly Ser Asn Ser Gly Asn Ile Gly Ser Leu Ser Thr Ile
                565                 570                 575
Pro Thr Ala Ala Pro Pro Ser Ser Thr Gly Val Arg Lys Gly Trp His
            580                 585                 590
Glu His Val Thr Gln Asp Leu Arg Ser His Leu Val His Lys Leu Val
        595                 600                 605
Gln Ala Ile Phe Pro Thr Pro Asp Pro Ala Ala Leu Lys Asp Arg Arg
    610                 615                 620
Met Glu Asn Leu Val Ala Tyr Ala Lys Lys Val Glu Gly Asp Met Tyr
625                 630                 635                 640
Glu Ser Ala Asn Ser Arg Asp Glu Tyr Tyr His Leu Leu Ala Glu Lys
                645                 650                 655
Ile Tyr Lys Ile Gln Lys Glu Leu Glu Glu Lys Arg Arg Thr Arg Leu
            660                 665                 670
His Lys Gln Gly Ile Leu Gly Asn Gln Pro Ala Leu Pro Ala Ser Gly
        675                 680                 685
Ala Gln Pro Pro Val Ile Pro Pro Ala Gln Ser Val Arg Pro Pro Asn
    690                 695                 700
Gly Pro Leu Pro Leu Pro Val Asn Arg Met Gln Val Ser Gln Gly Met
705                 710                 715                 720
Asn Ser Phe Asn Pro Met Ser Leu Gly Asn Val Gln Leu Pro Gln Ala
                725                 730                 735
Pro Met Gly Pro Arg Ala Ala Ser Pro Met Asn His Ser Val Gln Met
            740                 745                 750
Asn Ser Met Ala Ser Val Pro Gly Met Ala Ile Ser Pro Ser Arg Met
        755                 760                 765
Pro Gln Pro Pro Asn Met Met Gly Thr His Ala Asn Asn Ile Met Ala
    770                 775                 780
Gln Ala Pro Thr Gln Asn Gln Phe Leu Pro Gln Asn Gln Phe Pro Ser
785                 790                 795                 800
Ser Ser Gly Ala Met Ser Val Asn Ser Val Gly Met Gly Gln Pro Ala
                805                 810                 815
Ala Gln Ala Gly Val Ser Gln Gly Gln Glu Pro Gly Ala Ala Leu Pro
```

-continued

```
                820                 825                 830
Asn Pro Leu Asn Met Leu Ala Pro Gln Ala Ser Gln Leu Pro Cys Pro
            835                 840                 845
Pro Val Thr Gln Ser Pro Leu His Pro Thr Pro Pro Ala Ser Thr
850                 855                 860
Ala Ala Gly Met Pro Ser Leu Gln His Pro Thr Ala Pro Gly Met Thr
865                 870                 875                 880
Pro Pro Gln Pro Ala Ala Pro Thr Gln Pro Ser Thr Pro Val Ser Ser
                885                 890                 895
Gly Gln Thr Pro Thr Pro Thr Pro Gly Ser Val Pro Ser Ala Ala Gln
            900                 905                 910
Thr Gln Ser Thr Pro Thr Val Gln Ala Ala Gln Ala Gln Val Thr
            915                 920                 925
Pro Gln Pro Gln Thr Pro Val Gln Pro Pro Ser Val Ala Thr Pro Gln
930                 935                 940
Ser Ser Gln Gln Gln Pro Thr Pro Val His Thr Gln Pro Pro Gly Thr
945                 950                 955                 960
Pro Leu Ser Gln Ala Ala Ala Ser Ile Asp Asn Arg Val Pro Thr Pro
                965                 970                 975
Ser Thr Val Thr Ser Ala Glu Thr Ser Ser Gln Gln Pro Gly Pro Asp
            980                 985                 990
Val Pro Met Leu Glu Met Lys Thr Glu Val Gln Thr Asp Asp Ala Glu
            995                 1000                1005
Pro Glu  Pro Thr Glu Ser Lys  Gly Glu Pro Arg Ser  Glu Met Met
    1010                1015                1020
Glu Glu  Asp Leu Gln Gly Ser  Ser Gln Val Lys Glu  Glu Thr Asp
    1025                1030                1035
Thr Thr  Glu Gln Lys Ser Glu  Pro Met Glu Val Glu  Glu Lys Lys
    1040                1045                1050
Pro Glu  Val Lys Val Glu Ala  Lys Glu Glu Glu Glu  Asn Ser Ser
    1055                1060                1065
Asn Asp  Thr Ala Ser Gln Ser  Thr Ser Pro Ser Gln  Pro Arg Lys
    1070                1075                1080
Lys Ile Phe Lys Pro Glu Glu  Leu Arg Gln Ala Leu  Met Pro Thr
    1085                1090                1095
Leu Glu  Ala Leu Tyr Arg Gln  Asp Pro Glu Ser Leu  Pro Phe Arg
    1100                1105                1110
Gln Pro  Val Asp Pro Gln Leu  Leu Gly Ile Pro Asp  Tyr Phe Asp
    1115                1120                1125
Ile Val  Lys Asn Pro Met Asp  Leu Ser Thr Ile Lys  Arg Lys Leu
    1130                1135                1140
Asp Thr  Gly Gln Tyr Gln Glu  Pro Trp Gln Tyr Val  Asp Asp Val
    1145                1150                1155
Arg Leu  Met Phe Asn Asn Ala  Trp Leu Tyr Asn Arg  Lys Thr Ser
    1160                1165                1170
Arg Val  Tyr Lys Phe Cys Ser  Lys Leu Ala Glu Val  Phe Glu Gln
    1175                1180                1185
Glu Ile  Asp Pro Val Met Gln  Ser Leu Gly Tyr Cys  Cys Gly Arg
    1190                1195                1200
Lys Tyr  Glu Phe Ser Pro Gln  Thr Leu Cys Cys Tyr  Gly Lys Gln
    1205                1210                1215
Leu Cys  Thr Ile Pro Arg Asp  Ala Ala Tyr Tyr Ser  Tyr Gln Asn
    1220                1225                1230
```

-continued

```
Arg Tyr His Phe Cys Gly Lys Cys Phe Thr Glu Ile Gln Gly Glu
    1235            1240                1245
Asn Val Thr Leu Gly Asp Asp Pro Ser Gln Pro Gln Thr Thr Ile
    1250            1255                1260
Ser Lys Asp Gln Phe Glu Lys Lys Asn Asp Thr Leu Asp Pro
    1265            1270                1275
Glu Pro Phe Val Asp Cys Lys Glu Cys Gly Arg Lys Met His Gln
    1280            1285                1290
Ile Cys Val Leu His Tyr Asp Ile Ile Trp Pro Ser Gly Phe Val
    1295            1300                1305
Cys Asp Asn Cys Leu Lys Lys Thr Gly Arg Pro Arg Lys Glu Asn
    1310            1315                1320
Lys Phe Ser Ala Lys Arg Leu Gln Thr Thr Arg Leu Gly Asn His
    1325            1330                1335
Leu Glu Asp Arg Val Asn Lys Phe Leu Arg Arg Gln Asn His Pro
    1340            1345                1350
Glu Ala Gly Glu Val Phe Val Arg Val Val Ala Ser Ser Asp Lys
    1355            1360                1365
Thr Val Glu Val Lys Pro Gly Met Lys Ser Arg Phe Val Asp Ser
    1370            1375                1380
Gly Glu Met Ser Glu Ser Phe Pro Tyr Arg Thr Lys Ala Leu Phe
    1385            1390                1395
Ala Phe Glu Glu Ile Asp Gly Val Asp Val Cys Phe Phe Gly Met
    1400            1405                1410
His Val Gln Asp Thr Ala Leu Ile Ala Pro His Gln Ile Gln Gly
    1415            1420                1425
Cys Val Tyr Ile Ser Tyr Leu Asp Ser Ile His Phe Phe Arg Pro
    1430            1435                1440
Arg Cys Leu Arg Thr Ala Val Tyr His Glu Ile Leu Ile Gly Tyr
    1445            1450                1455
Leu Glu Tyr Val Lys Lys Leu Val Tyr Val Thr Ala His Ile Trp
    1460            1465                1470
Ala Cys Pro Pro Ser Glu Gly Asp Asp Tyr Ile Phe His Cys His
    1475            1480                1485
Pro Pro Asp Gln Lys Ile Pro Lys Pro Lys Arg Leu Gln Glu Trp
    1490            1495                1500
Tyr Lys Lys Met Leu Asp Lys Ala Phe Ala Glu Arg Ile Ile Asn
    1505            1510                1515
Asp Tyr Lys Asp Ile Phe Lys Gln Ala Asn Glu Asp Arg Leu Thr
    1520            1525                1530
Ser Ala Lys Glu Leu Pro Tyr Phe Glu Gly Asp Phe Trp Pro Asn
    1535            1540                1545
Val Leu Glu Glu Ser Ile Lys Glu Leu Glu Gln Glu Glu Glu Glu
    1550            1555                1560
Arg Lys Lys Glu Glu Ser Thr Ala Ala Ser Glu Thr Pro Glu Gly
    1565            1570                1575
Ser Gln Gly Asp Ser Lys Asn Ala Lys Lys Lys Asn Asn Lys Lys
    1580            1585                1590
Thr Asn Lys Asn Lys Ser Ser Ile Ser Arg Ala Asn Lys Lys Lys
    1595            1600                1605
Pro Ser Met Pro Asn Val Ser Asn Asp Leu Ser Gln Lys Leu Tyr
    1610            1615                1620
```

```
Ala Thr Met Glu Lys His Lys Glu Val Phe Phe Val Ile His Leu
1625                1630                1635

His Ala Gly Pro Val Ile Ser Thr Gln Pro Pro Ile Val Asp Pro
     1640                1645                1650

Asp Pro Leu Leu Ser Cys Asp Leu Met Asp Gly Arg Asp Ala Phe
     1655                1660                1665

Leu Thr Leu Ala Arg Asp Lys His Trp Glu Phe Ser Ser Leu Arg
     1670                1675                1680

Arg Ser Lys Trp Ser Thr Leu Cys Met Leu Val Glu Leu His Thr
     1685                1690                1695

Gln Gly Gln Asp Arg Phe Val Tyr Thr Cys Asn Glu Cys Lys His
     1700                1705                1710

His Val Glu Thr Arg Trp His Cys Thr Val Cys Glu Asp Tyr Asp
     1715                1720                1725

Leu Cys Ile Asn Cys Tyr Asn Thr Lys Ser His Thr His Lys Met
     1730                1735                1740

Val Lys Trp Gly Leu Gly Leu Asp Asp Glu Gly Ser Ser Gln Gly
     1745                1750                1755

Glu Pro Gln Ser Lys Ser Pro Gln Glu Ser Arg Arg Leu Ser Ile
     1760                1765                1770

Gln Arg Cys Ile Gln Ser Leu Val His Ala Cys Gln Cys Arg Asn
     1775                1780                1785

Ala Asn Cys Ser Leu Pro Ser Cys Gln Lys Met Lys Arg Val Val
     1790                1795                1800

Gln His Thr Lys Gly Cys Lys Arg Lys Thr Asn Gly Gly Cys Pro
     1805                1810                1815

Val Cys Lys Gln Leu Ile Ala Leu Cys Cys Tyr His Ala Lys His
     1820                1825                1830

Cys Gln Glu Asn Lys Cys Pro Val Pro Phe Cys Leu Asn Ile Lys
     1835                1840                1845

His Asn Val Arg Gln Gln Gln Ile Gln His Cys Leu Gln Gln Ala
     1850                1855                1860

Gln Leu Met Arg Arg Arg Met Ala Thr Met Asn Thr Arg Asn Val
     1865                1870                1875

Pro Gln Gln Ser Leu Pro Ser Pro Thr Ser Ala Pro Pro Gly Thr
     1880                1885                1890

Pro Thr Gln Gln Pro Ser Thr Pro Gln Thr Pro Gln Pro Pro Ala
     1895                1900                1905

Gln Pro Gln Pro Ser Pro Val Asn Met Ser Pro Ala Gly Phe Pro
     1910                1915                1920

Asn Val Ala Arg Thr Gln Pro Pro Thr Ile Val Ser Ala Gly Lys
     1925                1930                1935

Pro Thr Asn Gln Val Pro Ala Pro Pro Pro Ala Gln Pro Pro
     1940                1945                1950

Pro Ala Ala Val Glu Ala Ala Arg Gln Ile Glu Arg Glu Ala Gln
     1955                1960                1965

Gln Gln Gln His Leu Tyr Arg Ala Asn Ile Asn Asn Gly Met Pro
     1970                1975                1980

Pro Gly Arg Asp Gly Met Gly Thr Pro Gly Ser Gln Met Thr Pro
     1985                1990                1995

Val Gly Leu Asn Val Pro Arg Pro Asn Gln Val Ser Gly Pro Val
     2000                2005                2010

Met Ser Ser Met Pro Pro Gly Gln Trp Gln Gln Ala Pro Ile Pro
```

-continued

```
              2015                2020                2025
Gln Gln  Gln Pro Met Pro  Gly Met Pro Arg  Pro Val Met Ser Met
         2030                2035                2040
Gln Ala  Gln Ala Ala Val  Ala Gly Pro Arg  Met Pro Asn Val Gln
         2045                2050                2055
Pro Asn  Arg Ser Ile Ser  Pro Ser Ala Leu  Gln Asp Leu Leu Arg
         2060                2065                2070
Thr Leu  Lys Ser Pro Ser  Ser Pro Gln Gln  Gln Gln Val Leu
         2075                2080                2085
Asn Ile  Leu Lys Ser Asn  Pro Gln Leu Met  Ala Ala Phe Ile Lys
         2090                2095                2100
Gln Arg  Thr Ala Lys Tyr  Val Ala Asn Gln  Pro Gly Met Gln Pro
         2105                2110                2115
Gln Pro  Gly Leu Gln Ser  Gln Pro Gly Met  Gln Pro Gln Pro Gly
         2120                2125                2130
Met His  Gln Gln Pro Ser  Leu Gln Asn Leu  Asn Ala Met Gln Ala
         2135                2140                2145
Gly Val  Pro Arg Pro Gly  Val Pro Pro Gln  Pro Ala Met Gly
         2150                2155                2160
Gly Leu  Asn Pro Gln Gly  Gln Ala Leu Asn  Ile Met Asn Pro Gly
         2165                2170                2175
His Asn  Pro Asn Met Thr  Asn Met Asn Pro  Gln Tyr Arg Glu Met
         2180                2185                2190
Val Arg  Arg Gln Leu Leu  Gln His Gln Gln  Gln Gln Gln Gln Gln
         2195                2200                2205
Gln Gln  Gln Gln Gln Gln  Gln Asn Ser Ala  Ser Leu Ala Gly
         2210                2215                2220
Gly Met  Ala Gly His Ser  Gln Phe Gln Gln  Pro Gln Gly Pro Gly
         2225                2230                2235
Gly Tyr  Ala Pro Ala Met  Gln Gln Gln Arg  Met Gln Gln His Leu
         2240                2245                2250
Pro Ile  Gln Gly Ser Ser  Met Gly Gln Met  Ala Ala Pro Met Gly
         2255                2260                2265
Gln Leu  Gly Gln Met Gly  Gln Pro Gly Leu  Gly Ala Asp Ser Thr
         2270                2275                2280
Pro Asn  Ile Gln Gln Ala  Leu Gln Gln Arg  Ile Leu Gln Gln Gln
         2285                2290                2295
Gln Met  Lys Gln Gln Ile  Gly Ser Pro Gly  Gln Pro Asn Pro Met
         2300                2305                2310
Ser Pro  Gln Gln His Met  Leu Ser Gly Gln  Pro Gln Ala Ser His
         2315                2320                2325
Leu Pro  Gly Gln Gln Ile  Ala Thr Ser Leu  Ser Asn Gln Val Arg
         2330                2335                2340
Ser Pro  Ala Pro Val Gln  Ser Pro Arg Pro  Gln Ser Gln Pro Pro
         2345                2350                2355
His Ser  Ser Pro Ser Pro  Arg Ile Gln Pro  Gln Pro Ser Pro His
         2360                2365                2370
His Val  Ser Pro Gln Thr  Gly Thr Pro His  Pro Gly Leu Ala Val
         2375                2380                2385
Thr Met  Ala Ser Ser Met  Asp Gln Gly His  Leu Gly Asn Pro Glu
         2390                2395                2400
Gln Ser  Ala Met Leu Pro  Gln Leu Asn Thr  Pro Asn Arg Ser Ala
         2405                2410                2415
```

| | | |
|---|---|---|
| Leu Ser Ser Glu Leu Ser Leu Val Gly Asp Thr Thr Gly Asp Thr | | |
| 2420 2425 2430 | | |
| Leu Glu Lys Phe Val Glu Gly Leu | | |
| 2435 2440 | | |

<210> SEQ ID NO 9
<211> LENGTH: 8147
<212> TYPE: DNA
<213> ORGANISM: human
<220> FEATURE:
<221> NAME/KEY: CDS
<222> LOCATION: (819)..(8147)

<400> SEQUENCE: 9

| | |
|---|---|
| tccgaattcc tttttttaa ttgaggaatc aacagccgcc atcttgtcgc ggacccgacc | 60 |
| ggggcttcga gcgcgatcta ctcggccccg ccggtcccgg ccccacaac cgcccgcgca | 120 |
| ccccgctccg cccggccggc ccgctccgcc cggccctcgg cgcccgcccc ggcggccccg | 180 |
| ctcgcctctc ggctcggcct cccggagccc ggcggcggcg gcggcggcag cggcggcggc | 240 |
| ggcggcggaa cggggggtgg gggggccgcg gcggcggcgg cgaccccgct cggcgcattg | 300 |
| ttttccctca cggcggcggc ggcggcgggc cgcgggccgg gagcggagcc cggagccccc | 360 |
| tcgtcgtcgg gccgcgagcg aattcattaa gtggggcgcg ggggggagc gaggcggcgg | 420 |
| cggcggcggc accatgttct cggggactgc ctgagccgcc cggccgggcg ccgtcgctgc | 480 |
| cagccgggcc cggggggggcg gccgggccgc cggggcgccc ccaccgcgga gtgtcgcgct | 540 |
| cgggaggcgg gcaggggatg aggggggccgc ggccggcggc ggcggcggcg gccggggggcg | 600 |
| ggcggtgagc gctgcgggc gctgttgctg tggctgagat ttggccgccg cctcccccac | 660 |
| ccggcctgcg ccctccctct ccctcggcgc ccgcccgcgc cgctcgcggc gcccgcgctc | 720 |
| gctcctctcc ctcgcagccg gcagggcccc cgacccccgt ccgggccctc gccgccccgg | 780 |
| ccgcccgtgc ccggggctgt tttcgcgagc aggtgaaa atg gct gag aac ttg ctg | 836 |
| Met Ala Glu Asn Leu Leu | |
| 1 5 | |
| gac gga ccg ccc aac ccc aaa aga gcc aaa ctc agc tcg ccc ggt ttc | 884 |
| Asp Gly Pro Pro Asn Pro Lys Arg Ala Lys Leu Ser Ser Pro Gly Phe | |
| 10 15 20 | |
| tcg gcg aat gac agc aca gat ttt gga tca ttg ttt gac ttg gaa aat | 932 |
| Ser Ala Asn Asp Ser Thr Asp Phe Gly Ser Leu Phe Asp Leu Glu Asn | |
| 25 30 35 | |
| gat ctt cct gat gag ctg ata ccc aat gga gga gaa tta ggc ctt tta | 980 |
| Asp Leu Pro Asp Glu Leu Ile Pro Asn Gly Gly Glu Leu Gly Leu Leu | |
| 40 45 50 | |
| aac agt ggg aac ctt gtt cca gat gct gct tcc aaa cat aaa caa ctg | 1028 |
| Asn Ser Gly Asn Leu Val Pro Asp Ala Ala Ser Lys His Lys Gln Leu | |
| 55 60 65 70 | |
| tcg gag ctt cta cga gga ggc agc ggc tct agt atc aac cca gga ata | 1076 |
| Ser Glu Leu Leu Arg Gly Gly Ser Gly Ser Ser Ile Asn Pro Gly Ile | |
| 75 80 85 | |
| gga aat gtg agc gcc agc agc ccc gtg cag cag ggc ctg ggt ggc cag | 1124 |
| Gly Asn Val Ser Ala Ser Ser Pro Val Gln Gln Gly Leu Gly Gly Gln | |
| 90 95 100 | |
| gct caa ggg cag ccg aac agt gct aac atg gcc agc ctc agt gcc atg | 1172 |
| Ala Gln Gly Gln Pro Asn Ser Ala Asn Met Ala Ser Leu Ser Ala Met | |
| 105 110 115 | |
| ggc aag agc cct ctg agc cag gga gat tct tca gcc ccc agc ctg cct | 1220 |
| Gly Lys Ser Pro Leu Ser Gln Gly Asp Ser Ser Ala Pro Ser Leu Pro | |
| 120 125 130 | |

-continued

| | |
|---|---|
| aaa cag gca gcc agc acc tct ggg ccc acc ccc gct gcc tcc caa gca<br>Lys Gln Ala Ala Ser Thr Ser Gly Pro Thr Pro Ala Ala Ser Gln Ala<br>135                140                      145                      150 | 1268 |
| ctg aat ccg caa gca caa aag caa gtg ggg ctg gcg act agc agc cct<br>Leu Asn Pro Gln Ala Gln Lys Gln Val Gly Leu Ala Thr Ser Ser Pro<br>                    155                      160                      165 | 1316 |
| gcc acg tca cag act gga cct ggt atc tgc atg aat gct aac ttt aac<br>Ala Thr Ser Gln Thr Gly Pro Gly Ile Cys Met Asn Ala Asn Phe Asn<br>            170                      175                      180 | 1364 |
| cag acc cac cca ggc ctc ctc aat agt aac tct ggc cat agc tta att<br>Gln Thr His Pro Gly Leu Leu Asn Ser Asn Ser Gly His Ser Leu Ile<br>                    185                      190                      195 | 1412 |
| aat cag gct tca caa ggg cag gcg caa gtc atg aat gga tct ctt ggg<br>Asn Gln Ala Ser Gln Gly Gln Ala Gln Val Met Asn Gly Ser Leu Gly<br>200                205                      210 | 1460 |
| gct gct ggc aga gga agg gga gct gga atg ccg tac cct act cca gcc<br>Ala Ala Gly Arg Gly Arg Gly Ala Gly Met Pro Tyr Pro Thr Pro Ala<br>215                220                      225                      230 | 1508 |
| atg cag ggc gcc tcg agc agc gtg ctg gct gag acc cta acg cag gtt<br>Met Gln Gly Ala Ser Ser Ser Val Leu Ala Glu Thr Leu Thr Gln Val<br>                    235                      240                      245 | 1556 |
| tcc ccg caa atg act ggt cac gcg gga ctg aac acc gca cag gca gga<br>Ser Pro Gln Met Thr Gly His Ala Gly Leu Asn Thr Ala Gln Ala Gly<br>            250                      255                      260 | 1604 |
| ggc atg gcc aag atg gga ata act ggg aac aca agt cca ttt gga cag<br>Gly Met Ala Lys Met Gly Ile Thr Gly Asn Thr Ser Pro Phe Gly Gln<br>265                270                      275 | 1652 |
| ccc ttt agt caa gct gga ggg cag cca atg gga gcc act gga gtg aac<br>Pro Phe Ser Gln Ala Gly Gly Gln Pro Met Gly Ala Thr Gly Val Asn<br>280                      285                      290 | 1700 |
| ccc cag tta gcc agc aaa cag agc atg gtc aac agt ttg ccc acc ttc<br>Pro Gln Leu Ala Ser Lys Gln Ser Met Val Asn Ser Leu Pro Thr Phe<br>295                300                      305                      310 | 1748 |
| cct aca gat atc aag aat act tca gtc acc aac gtg cca aat atg tct<br>Pro Thr Asp Ile Lys Asn Thr Ser Val Thr Asn Val Pro Asn Met Ser<br>                    315                      320                      325 | 1796 |
| cag atg caa aca tca gtg gga att gta ccc aca caa gca att gca aca<br>Gln Met Gln Thr Ser Val Gly Ile Val Pro Thr Gln Ala Ile Ala Thr<br>            330                      335                      340 | 1844 |
| ggc ccc act gca gat cct gaa aaa cgc aaa ctg ata cag cag cag ctg<br>Gly Pro Thr Ala Asp Pro Glu Lys Arg Lys Leu Ile Gln Gln Gln Leu<br>345                350                      355 | 1892 |
| gtt cta ctg ctt cat gct cat aag tgt cag aga cga gag caa gca aac<br>Val Leu Leu Leu His Ala His Lys Cys Gln Arg Arg Glu Gln Ala Asn<br>360                365                      370 | 1940 |
| gga gag gtt cgg gcc tgc tcg ctc ccg cat tgt cga acc atg aaa aac<br>Gly Glu Val Arg Ala Cys Ser Leu Pro His Cys Arg Thr Met Lys Asn<br>375                380                      385                      390 | 1988 |
| gtt ttg aat cac atg acg cat tgt cag gct ggg aaa gcc tgc caa gtt<br>Val Leu Asn His Met Thr His Cys Gln Ala Gly Lys Ala Cys Gln Val<br>                    395                      400                      405 | 2036 |
| gcc cat tgt gca tct tca cga caa atc atc tct cat tgg aag aac tgc<br>Ala His Cys Ala Ser Ser Arg Gln Ile Ile Ser His Trp Lys Asn Cys<br>            410                      415                      420 | 2084 |
| aca cga cat gac tgt cct gtt tgc ctc cct ttg aaa aat gcc agt gac<br>Thr Arg His Asp Cys Pro Val Cys Leu Pro Leu Lys Asn Ala Ser Asp<br>425                430                      435 | 2132 |
| aag cga aac caa caa acc atc ctg ggg tct cca gct agt gga att caa<br>Lys Arg Asn Gln Gln Thr Ile Leu Gly Ser Pro Ala Ser Gly Ile Gln | 2180 |

```
                    440                 445                 450
aac aca att ggt tct gtt ggc aca ggg caa cag aat gcc act tct tta       2228
Asn Thr Ile Gly Ser Val Gly Thr Gly Gln Gln Asn Ala Thr Ser Leu
455                 460                 465                 470 agt aac cca aat ccc ata gac ccc agc tcc atg cag cga gcc tat gct       2276
Ser Asn Pro Asn Pro Ile Asp Pro Ser Ser Met Gln Arg Ala Tyr Ala
                475                 480                 485 gct ctc gga ctc ccc tac atg aac cag ccc cag acg cag ctg cag cct       2324
Ala Leu Gly Leu Pro Tyr Met Asn Gln Pro Gln Thr Gln Leu Gln Pro
            490                 495                 500 cag gtt cct ggc cag caa cca gca cag cct caa acc cac cag cag atg       2372
Gln Val Pro Gly Gln Gln Pro Ala Gln Pro Gln Thr His Gln Gln Met
        505                 510                 515 agg act ctc aac ccc ctg gga aat aat cca atg aac att cca gca gga       2420
Arg Thr Leu Asn Pro Leu Gly Asn Asn Pro Met Asn Ile Pro Ala Gly
    520                 525                 530 gga ata aca aca gat cag cag ccc cca aac ttg att tca gaa tca gct       2468
Gly Ile Thr Thr Asp Gln Gln Pro Pro Asn Leu Ile Ser Glu Ser Ala
535                 540                 545                 550 ctt ccg act tcc ctg ggg gcc aca aac cca ctg atg aac gat ggc tcc       2516
Leu Pro Thr Ser Leu Gly Ala Thr Asn Pro Leu Met Asn Asp Gly Ser
                555                 560                 565 aac tct ggt aac att gga acc ctc agc act ata cca aca gca gct cct       2564
Asn Ser Gly Asn Ile Gly Thr Leu Ser Thr Ile Pro Thr Ala Ala Pro
            570                 575                 580 cct tct agc acc ggt gta agg aaa ggc tgg cac gaa cat gtc act cag       2612
Pro Ser Ser Thr Gly Val Arg Lys Gly Trp His Glu His Val Thr Gln
        585                 590                 595 gac ctg cgg agc cat cta gtg cat aaa ctc gtc caa gcc atc ttc cca       2660
Asp Leu Arg Ser His Leu Val His Lys Leu Val Gln Ala Ile Phe Pro
    600                 605                 610 aca cct gat ccc gca gct cta aag gat cgc cgc atg gaa aac ctg gta       2708
Thr Pro Asp Pro Ala Ala Leu Lys Asp Arg Arg Met Glu Asn Leu Val
615                 620                 625                 630 gcc tat gct aag aaa gtg gaa ggg gac atg tac gag tct gcc aac agc       2756
Ala Tyr Ala Lys Lys Val Glu Gly Asp Met Tyr Glu Ser Ala Asn Ser
                635                 640                 645 agg gat gaa tat tat cac tta tta gca gag aaa atc tac aag ata caa       2804
Arg Asp Glu Tyr Tyr His Leu Leu Ala Glu Lys Ile Tyr Lys Ile Gln
            650                 655                 660 aaa gaa cta gaa gaa aaa cgg agg tcg cgt tta cat aaa caa ggc atc       2852
Lys Glu Leu Glu Glu Lys Arg Arg Ser Arg Leu His Lys Gln Gly Ile
        665                 670                 675 ttg ggg aac cag cca gcc tta cca gcc ccg ggg gct cag ccc cct gtg       2900
Leu Gly Asn Gln Pro Ala Leu Pro Ala Pro Gly Ala Gln Pro Pro Val
    680                 685                 690 att cca cag gca caa cct gtg aga cct cca aat gga ccc ctg tcc ctg       2948
Ile Pro Gln Ala Gln Pro Val Arg Pro Pro Asn Gly Pro Leu Ser Leu
695                 700                 705                 710 cca gtg aat cgc atg caa gtt tct caa ggg atg aat tca ttt aac ccc       2996
Pro Val Asn Arg Met Gln Val Ser Gln Gly Met Asn Ser Phe Asn Pro
                715                 720                 725 atg tcc ttg ggg aac gtc cag ttg cca caa gca ccc atg gga cct cgt       3044
Met Ser Leu Gly Asn Val Gln Leu Pro Gln Ala Pro Met Gly Pro Arg
            730                 735                 740 gca gcc tcc cca atg aac cac tct gtc cag atg aac agc atg ggc tca       3092
Ala Ala Ser Pro Met Asn His Ser Val Gln Met Asn Ser Met Gly Ser
        745                 750                 755 gtg cca ggg atg gcc att tct cct tcc cga atg cct cag cct ccg aac       3140
```

-continued

```
                Val Pro Gly Met Ala Ile Ser Pro Ser Arg Met Pro Gln Pro Pro Asn
                                760                 765                 770 atg atg ggt gca cac acc aac aac atg atg gcc cag gcg ccc gct cag            3188
Met Met Gly Ala His Thr Asn Asn Met Met Ala Gln Ala Pro Ala Gln
775                 780                 785                 790 agc cag ttt ctg cca cag aac cag ttc ccg tca tcc agc ggg gcg atg            3236
Ser Gln Phe Leu Pro Gln Asn Gln Phe Pro Ser Ser Ser Gly Ala Met
                795                 800                 805 agt gtg ggc atg ggg cag ccg cca gcc caa aca ggc gtg tca cag gga            3284
Ser Val Gly Met Gly Gln Pro Pro Ala Gln Thr Gly Val Ser Gln Gly
            810                 815                 820 cag gtg cct ggt gct gct ctt cct aac cct ctc aac atg ctg ggg cct            3332
Gln Val Pro Gly Ala Ala Leu Pro Asn Pro Leu Asn Met Leu Gly Pro
        825                 830                 835 cag gcc agc cag cta cct tgc cct cca gtg aca cag tca cca ctg cac            3380
Gln Ala Ser Gln Leu Pro Cys Pro Pro Val Thr Gln Ser Pro Leu His
    840                 845                 850 cca aca ccg cct cct gct tcc acg gct gct ggc atg cca tct ctc cag            3428
Pro Thr Pro Pro Pro Ala Ser Thr Ala Ala Gly Met Pro Ser Leu Gln
855                 860                 865                 870 cac acg aca cca cct ggg atg act cct ccc cag cca gca gct ccc act            3476
His Thr Thr Pro Pro Gly Met Thr Pro Pro Gln Pro Ala Ala Pro Thr
                875                 880                 885 cag cca tca act cct gtg tcg tct tcc ggg cag act ccc acc ccg act            3524
Gln Pro Ser Thr Pro Val Ser Ser Ser Gly Gln Thr Pro Thr Pro Thr
                890                 895                 900 cct ggc tca gtg ccc agt gct acc caa acc cag agc acc cct aca gtc            3572
Pro Gly Ser Val Pro Ser Ala Thr Gln Thr Gln Ser Thr Pro Thr Val
            905                 910                 915 cag gca gca gcc cag gcc cag gtg acc ccg cag cct caa acc cca gtt            3620
Gln Ala Ala Ala Gln Ala Gln Val Thr Pro Gln Pro Gln Thr Pro Val
        920                 925                 930 cag ccc ccg tct gtg gct acc cct cag tca tcg cag caa cag ccg acg            3668
Gln Pro Pro Ser Val Ala Thr Pro Gln Ser Ser Gln Gln Gln Pro Thr
935                 940                 945                 950 cct gtg cac gcc cag cct cct ggc aca ccg ctt tcc cag gca gca gcc            3716
Pro Val His Ala Gln Pro Pro Gly Thr Pro Leu Ser Gln Ala Ala Ala
                955                 960                 965 agc att gat aac aga gtc cct acc ccc tcc tcg gtg gcc agc gca gaa            3764
Ser Ile Asp Asn Arg Val Pro Thr Pro Ser Ser Val Ala Ser Ala Glu
                970                 975                 980 acc aat tcc cag cag cca gga cct gac gta cct gtg ctg gaa atg aag            3812
Thr Asn Ser Gln Gln Pro Gly Pro Asp Val Pro Val Leu Glu Met Lys
            985                 990                 995 acg gag  acc caa gca gag gac  act gag ccc gat cct  ggt gaa tcc            3857
Thr Glu  Thr Gln Ala Glu Asp  Thr Glu Pro Asp Pro  Gly Glu Ser
        1000                1005                1010 aaa ggg gag ccc agg tct gag  atg atg gag gag gat  ttg caa gga            3902
Lys Gly Glu Pro Arg Ser Glu  Met Met Glu Glu Asp  Leu Gln Gly
    1015                1020                1025 gct tcc caa gtt aaa gaa gaa  aca gac ata gca gag  cag aaa tca            3947
Ala Ser Gln Val Lys Glu Glu  Thr Asp Ile Ala Glu  Gln Lys Ser
    1030                1035                1040 gaa cca atg gaa gtg gat gaa  aag aaa cct gaa gtg  aaa gta gaa            3992
Glu Pro Met Glu Val Asp Glu  Lys Lys Pro Glu Val  Lys Val Glu
    1045                1050                1055 gtt aaa gag gaa gaa gag agt  agc agt aac ggc aca  gcc tct cag            4037
Val Lys Glu Glu Glu Glu Ser  Ser Ser Asn Gly Thr  Ala Ser Gln
    1060                1065                1070
```

```
tca aca tct cct tcg cag ccg cgc aaa aaa atc ttt aaa cca gag      4082
Ser Thr Ser Pro Ser Gln Pro Arg Lys Lys Ile Phe Lys Pro Glu
    1075            1080                1085 gag tta cgc cag gcc ctc atg cca acc cta gaa gca ctg tat cga      4127
Glu Leu Arg Gln Ala Leu Met Pro Thr Leu Glu Ala Leu Tyr Arg
    1090            1095                1100 cag gac cca gag tca tta cct ttc cgg cag cct gta gat ccc cag      4172
Gln Asp Pro Glu Ser Leu Pro Phe Arg Gln Pro Val Asp Pro Gln
    1105            1110                1115 ctc ctc gga att cca gac tat ttt gac atc gta aag aat ccc atg      4217
Leu Leu Gly Ile Pro Asp Tyr Phe Asp Ile Val Lys Asn Pro Met
    1120            1125                1130 gac ctc tcc acc atc aag cgg aag ctg gac aca ggg caa tac caa      4262
Asp Leu Ser Thr Ile Lys Arg Lys Leu Asp Thr Gly Gln Tyr Gln
    1135            1140                1145 gag ccc tgg cag tac gtg gac gac gtc tgg ctc atg ttc aac aat      4307
Glu Pro Trp Gln Tyr Val Asp Asp Val Trp Leu Met Phe Asn Asn
    1150            1155                1160 gcc tgg ctc tat aat cgc aag aca tcc cga gtc tat aag ttt tgc      4352
Ala Trp Leu Tyr Asn Arg Lys Thr Ser Arg Val Tyr Lys Phe Cys
    1165            1170                1175 agt aag ctt gca gag gtc ttt gag cag gaa att gac cct gtc atg      4397
Ser Lys Leu Ala Glu Val Phe Glu Gln Glu Ile Asp Pro Val Met
    1180            1185                1190 cag tcc ctt gga tat tgc tgt gga cgc aag tat gag ttt tcc cca      4442
Gln Ser Leu Gly Tyr Cys Cys Gly Arg Lys Tyr Glu Phe Ser Pro
    1195            1200                1205 cag act ttg tgc tgc tat ggg aag cag ctg tgt acc att cct cgc      4487
Gln Thr Leu Cys Cys Tyr Gly Lys Gln Leu Cys Thr Ile Pro Arg
    1210            1215                1220 gat gct gcc tac tac agc tat cag aat agg tat cat ttc tgt gag      4532
Asp Ala Ala Tyr Tyr Ser Tyr Gln Asn Arg Tyr His Phe Cys Glu
    1225            1230                1235 aag tgt ttc aca gag atc cag ggc gag aat gtg acc ctg ggt gac      4577
Lys Cys Phe Thr Glu Ile Gln Gly Glu Asn Val Thr Leu Gly Asp
    1240            1245                1250 gac cct tca cag ccc cag acg aca att tca aag gat cag ttt gaa      4622
Asp Pro Ser Gln Pro Gln Thr Thr Ile Ser Lys Asp Gln Phe Glu
    1255            1260                1265 aag aag aaa aat gat acc tta gac ccc gaa cct ttc gtt gat tgc      4667
Lys Lys Lys Asn Asp Thr Leu Asp Pro Glu Pro Phe Val Asp Cys
    1270            1275                1280 aag gag tgt ggc cgg aag atg cat cag att tgc gtt ctg cac tat      4712
Lys Glu Cys Gly Arg Lys Met His Gln Ile Cys Val Leu His Tyr
    1285            1290                1295 gac atc att tgg cct tca ggt ttt gtg tgc gac aac tgc ttg aag      4757
Asp Ile Ile Trp Pro Ser Gly Phe Val Cys Asp Asn Cys Leu Lys
    1300            1305                1310 aaa act ggc aga cct cga aaa gaa aac aaa ttc agt gct aag agg      4802
Lys Thr Gly Arg Pro Arg Lys Glu Asn Lys Phe Ser Ala Lys Arg
    1315            1320                1325 ctg cag acc aca aga ctg gga aac cac ttg gaa gac cga gtg aac      4847
Leu Gln Thr Thr Arg Leu Gly Asn His Leu Glu Asp Arg Val Asn
    1330            1335                1340 aaa ttt ttg cgg cgc cag aat cac cct gaa gcc ggg gag gtt ttt      4892
Lys Phe Leu Arg Arg Gln Asn His Pro Glu Ala Gly Glu Val Phe
    1345            1350                1355 gtc cga gtg gtg gcc agc tca gac aag acg gtg gag gtc aag ccc      4937
Val Arg Val Val Ala Ser Ser Asp Lys Thr Val Glu Val Lys Pro
    1360            1365                1370
```

| | | |
|---|---|---|
| ggg atg aag tca cgg ttt gtg gat tct ggg gaa atg tct gaa tct<br>Gly Met Lys Ser Arg Phe Val Asp Ser Gly Glu Met Ser Glu Ser<br>1375 1380 1385 | | 4982 |
| ttc cca tat cga acc aaa gct ctg ttt gct ttt gag gaa att gac<br>Phe Pro Tyr Arg Thr Lys Ala Leu Phe Ala Phe Glu Glu Ile Asp<br>1390 1395 1400 | | 5027 |
| ggc gtg gat gtc tgc ttt ttt gga atg cac gtc caa gaa tac ggc<br>Gly Val Asp Val Cys Phe Phe Gly Met His Val Gln Glu Tyr Gly<br>1405 1410 1415 | | 5072 |
| tct gat tgc ccc cct cca aac acg agg cgt gta tac att tct tat<br>Ser Asp Cys Pro Pro Pro Asn Thr Arg Arg Val Tyr Ile Ser Tyr<br>1420 1425 1430 | | 5117 |
| ctg gat agt att cat ttc ttc cgg cca cgt tgc ctc cgc aca gcc<br>Leu Asp Ser Ile His Phe Phe Arg Pro Arg Cys Leu Arg Thr Ala<br>1435 1440 1445 | | 5162 |
| gtt tac cat gag atc ctt att gga tat tta gag tat gtg aag aaa<br>Val Tyr His Glu Ile Leu Ile Gly Tyr Leu Glu Tyr Val Lys Lys<br>1450 1455 1460 | | 5207 |
| tta ggg tat gtg aca ggg cac atc tgg gcc tgt cct cca agt gaa<br>Leu Gly Tyr Val Thr Gly His Ile Trp Ala Cys Pro Pro Ser Glu<br>1465 1470 1475 | | 5252 |
| gga gat gat tac atc ttc cat tgc cac cca cct gat caa aaa ata<br>Gly Asp Asp Tyr Ile Phe His Cys His Pro Pro Asp Gln Lys Ile<br>1480 1485 1490 | | 5297 |
| ccc aag cca aaa cga ctg cag gag tgg tac aaa aag atg ctg gac<br>Pro Lys Pro Lys Arg Leu Gln Glu Trp Tyr Lys Lys Met Leu Asp<br>1495 1500 1505 | | 5342 |
| aag gcg ttt gca gag cgg atc atc cat gac tac aag gat att ttc<br>Lys Ala Phe Ala Glu Arg Ile Ile His Asp Tyr Lys Asp Ile Phe<br>1510 1515 1520 | | 5387 |
| aaa caa gca act gaa gac agg ctc acc agt gcc aag gaa ctg ccc<br>Lys Gln Ala Thr Glu Asp Arg Leu Thr Ser Ala Lys Glu Leu Pro<br>1525 1530 1535 | | 5432 |
| tat ttt gaa ggt gat ttc tgg ccc aat gtg tta gaa gag agc att<br>Tyr Phe Glu Gly Asp Phe Trp Pro Asn Val Leu Glu Glu Ser Ile<br>1540 1545 1550 | | 5477 |
| aag gaa cta gaa caa gaa gaa gag gag agg aaa aag gaa gag agc<br>Lys Glu Leu Glu Gln Glu Glu Glu Glu Arg Lys Lys Glu Glu Ser<br>1555 1560 1565 | | 5522 |
| act gca gcc agt gaa acc act gag ggc agt cag ggc gac agc aag<br>Thr Ala Ala Ser Glu Thr Thr Glu Gly Ser Gln Gly Asp Ser Lys<br>1570 1575 1580 | | 5567 |
| aat gcc aag aag aag aac aac aag aaa acc aac aag aac aaa agc<br>Asn Ala Lys Lys Lys Asn Asn Lys Lys Thr Asn Lys Asn Lys Ser<br>1585 1590 1595 | | 5612 |
| agc atc agc cgc gcc aac aag aag aag ccc agc atg ccc aac gtg<br>Ser Ile Ser Arg Ala Asn Lys Lys Lys Pro Ser Met Pro Asn Val<br>1600 1605 1610 | | 5657 |
| tcc aat gac ctg tcc cag aag ctg tat gcc acc atg gag aag cac<br>Ser Asn Asp Leu Ser Gln Lys Leu Tyr Ala Thr Met Glu Lys His<br>1615 1620 1625 | | 5702 |
| aag gag gtc ttc ttc gtg atc cac ctg cac gct ggg cct gtc atc<br>Lys Glu Val Phe Phe Val Ile His Leu His Ala Gly Pro Val Ile<br>1630 1635 1640 | | 5747 |
| aac acc ctg ccc ccc atc gtc gac ccc gac ccc ctg ctc agc tgt<br>Asn Thr Leu Pro Pro Ile Val Asp Pro Asp Pro Leu Leu Ser Cys<br>1645 1650 1655 | | 5792 |
| gac ctc atg gat ggg cgc gac gcc ttc ctc acc ctc gcc aga gac<br>Asp Leu Met Asp Gly Arg Asp Ala Phe Leu Thr Leu Ala Arg Asp | | 5837 |

-continued

| | | | | | | | | | | |
|---|---|---|---|---|---|---|---|---|---|---|
| | 1660 | | | 1665 | | | 1670 | | | |
| aag | cac | tgg | gag | ttc | tcc | tcc | ttg | cgc | cgc | tcc | aag | tgg | tcc | acg | 5882 |
| Lys | His | Trp | Glu | Phe | Ser | Ser | Leu | Arg | Arg | Ser | Lys | Trp | Ser | Thr | |
| 1675 | | | | 1680 | | | | 1685 | | | |
| ctc | tgc | atg | ctg | gtg | gag | ctg | cac | acc | cag | ggc | cag | gac | cgc | ttt | 5927 |
| Leu | Cys | Met | Leu | Val | Glu | Leu | His | Thr | Gln | Gly | Gln | Asp | Arg | Phe | |
| 1690 | | | | 1695 | | | | 1700 | | | |
| gtc | tac | acc | tgc | aac | gag | tgc | aag | cac | cac | gtg | gag | acg | cgc | tgg | 5972 |
| Val | Tyr | Thr | Cys | Asn | Glu | Cys | Lys | His | His | Val | Glu | Thr | Arg | Trp | |
| 1705 | | | | 1710 | | | | 1715 | | | |
| cac | tgc | act | gtg | tgc | gag | gac | tac | gac | ctc | tgc | atc | aac | tgc | tat | 6017 |
| His | Cys | Thr | Val | Cys | Glu | Asp | Tyr | Asp | Leu | Cys | Ile | Asn | Cys | Tyr | |
| 1720 | | | | 1725 | | | | 1730 | | | |
| aac | acg | aag | agc | cat | gcc | cat | aag | atg | gtg | aag | tgg | ggg | ctg | ggc | 6062 |
| Asn | Thr | Lys | Ser | His | Ala | His | Lys | Met | Val | Lys | Trp | Gly | Leu | Gly | |
| 1735 | | | | 1740 | | | | 1745 | | | |
| ctg | gat | gac | gag | ggc | agc | agc | cag | ggc | gag | cca | cag | tca | aag | agc | 6107 |
| Leu | Asp | Asp | Glu | Gly | Ser | Ser | Gln | Gly | Glu | Pro | Gln | Ser | Lys | Ser | |
| 1750 | | | | 1755 | | | | 1760 | | | |
| ccc | cag | gag | tca | cgc | cgg | ctg | agc | atc | cag | cgc | tgc | atc | cag | tcg | 6152 |
| Pro | Gln | Glu | Ser | Arg | Arg | Leu | Ser | Ile | Gln | Arg | Cys | Ile | Gln | Ser | |
| 1765 | | | | 1770 | | | | 1775 | | | |
| ctg | gtg | cac | gcg | tgc | cag | tgc | cgc | aac | gcc | aac | tgc | tcg | ctg | cca | 6197 |
| Leu | Val | His | Ala | Cys | Gln | Cys | Arg | Asn | Ala | Asn | Cys | Ser | Leu | Pro | |
| 1780 | | | | 1785 | | | | 1790 | | | |
| tcc | tgc | cag | aag | atg | aag | cgg | gtg | gtg | cag | cac | acc | aag | ggc | tgc | 6242 |
| Ser | Cys | Gln | Lys | Met | Lys | Arg | Val | Val | Gln | His | Thr | Lys | Gly | Cys | |
| 1795 | | | | 1800 | | | | 1805 | | | |
| aaa | cgc | aag | acc | aac | ggg | ggc | tgc | ccg | gtg | tgc | aag | cag | ctc | atc | 6287 |
| Lys | Arg | Lys | Thr | Asn | Gly | Gly | Cys | Pro | Val | Cys | Lys | Gln | Leu | Ile | |
| 1810 | | | | 1815 | | | | 1820 | | | |
| gcc | ctc | tgc | tgc | tac | cac | gcc | aag | cac | tgc | caa | gaa | aac | aaa | tgc | 6332 |
| Ala | Leu | Cys | Cys | Tyr | His | Ala | Lys | His | Cys | Gln | Glu | Asn | Lys | Cys | |
| 1825 | | | | 1830 | | | | 1835 | | | |
| ccc | gtg | ccc | ttc | tgc | ctc | aac | atc | aaa | cac | aag | ctc | cgc | cag | cag | 6377 |
| Pro | Val | Pro | Phe | Cys | Leu | Asn | Ile | Lys | His | Lys | Leu | Arg | Gln | Gln | |
| 1840 | | | | 1845 | | | | 1850 | | | |
| cag | atc | cag | cac | cgc | ctg | cag | cag | gcc | cag | ctc | atg | cgc | cgg | cgg | 6422 |
| Gln | Ile | Gln | His | Arg | Leu | Gln | Gln | Ala | Gln | Leu | Met | Arg | Arg | Arg | |
| 1855 | | | | 1860 | | | | 1865 | | | |
| atg | gcc | acc | atg | aac | acc | cgc | aac | gtg | cct | cag | cag | agt | ctg | cct | 6467 |
| Met | Ala | Thr | Met | Asn | Thr | Arg | Asn | Val | Pro | Gln | Gln | Ser | Leu | Pro | |
| 1870 | | | | 1875 | | | | 1880 | | | |
| tct | cct | acc | tca | gca | ccg | ccc | ggg | acc | ccc | aca | cag | cag | ccc | agc | 6512 |
| Ser | Pro | Thr | Ser | Ala | Pro | Pro | Gly | Thr | Pro | Thr | Gln | Gln | Pro | Ser | |
| 1885 | | | | 1890 | | | | 1895 | | | |
| aca | ccc | cag | acg | ccg | cag | ccc | cct | gcc | cag | ccc | caa | ccc | tca | ccc | 6557 |
| Thr | Pro | Gln | Thr | Pro | Gln | Pro | Pro | Ala | Gln | Pro | Gln | Pro | Ser | Pro | |
| 1900 | | | | 1905 | | | | 1910 | | | |
| gtg | agc | atg | tca | cca | gct | ggc | ttc | ccc | agc | gtg | gcc | cgg | act | cag | 6602 |
| Val | Ser | Met | Ser | Pro | Ala | Gly | Phe | Pro | Ser | Val | Ala | Arg | Thr | Gln | |
| 1915 | | | | 1920 | | | | 1925 | | | |
| ccc | ccc | acc | acg | gtg | tcc | aca | ggg | aag | cct | acc | agc | cag | gtg | ccg | 6647 |
| Pro | Pro | Thr | Thr | Val | Ser | Thr | Gly | Lys | Pro | Thr | Ser | Gln | Val | Pro | |
| 1930 | | | | 1935 | | | | 1940 | | | |
| gcc | ccc | cca | ccc | ccg | gcc | cag | ccc | cct | cct | gca | gcg | gtg | gaa | gcg | 6692 |
| Ala | Pro | Pro | Pro | Pro | Ala | Gln | Pro | Pro | Pro | Ala | Ala | Val | Glu | Ala | |
| 1945 | | | | 1950 | | | | 1955 | | | |
| gct | cgg | cag | atc | gag | cgt | gag | gcc | cag | cag | cag | cag | cac | ctg | tac | 6737 |

```
Ala Arg Gln Ile Glu Arg Glu Ala Gln Gln Gln His Leu Tyr
    1960            1965            1970 cgg gtg aac atc aac aac agc atg ccc cca gga cgc acg ggc atg        6782
Arg Val Asn Ile Asn Asn Ser Met Pro Pro Gly Arg Thr Gly Met
    1975            1980            1985 ggg acc ccg ggg agc cag atg gcc ccc gtg agc ctg aat gtg ccc        6827
Gly Thr Pro Gly Ser Gln Met Ala Pro Val Ser Leu Asn Val Pro
    1990            1995            2000 cga ccc aac cag gtg agc ggg ccc gtc atg ccc agc atg cct ccc        6872
Arg Pro Asn Gln Val Ser Gly Pro Val Met Pro Ser Met Pro Pro
    2005            2010            2015 ggg cag tgg cag cag gcg ccc ctt ccc cag cag cag ccc atg cca        6917
Gly Gln Trp Gln Gln Ala Pro Leu Pro Gln Gln Gln Pro Met Pro
    2020            2025            2030 ggc ttg ccc agg cct gtg ata tcc atg cag gcc cag gcg gcc gtg        6962
Gly Leu Pro Arg Pro Val Ile Ser Met Gln Ala Gln Ala Ala Val
    2035            2040            2045 gct ggg ccc cgg atg ccc agc gtg cag cca ccc agg agc atc tca        7007
Ala Gly Pro Arg Met Pro Ser Val Gln Pro Pro Arg Ser Ile Ser
    2050            2055            2060 ccc agc gct ctg caa gac ctg ctg cgg acc ctg aag tcg ccc agc        7052
Pro Ser Ala Leu Gln Asp Leu Leu Arg Thr Leu Lys Ser Pro Ser
    2065            2070            2075 tcc cct cag cag caa cag cag gtg ctg aac att ctc aaa tca aac        7097
Ser Pro Gln Gln Gln Gln Gln Val Leu Asn Ile Leu Lys Ser Asn
    2080            2085            2090 ccg cag cta atg gca gct ttc atc aaa cag cgc aca gcc aag tac        7142
Pro Gln Leu Met Ala Ala Phe Ile Lys Gln Arg Thr Ala Lys Tyr
    2095            2100            2105 gtg gcc aat cag ccc ggc atg cag ccc cag cct ggc ctc cag tcc        7187
Val Ala Asn Gln Pro Gly Met Gln Pro Gln Pro Gly Leu Gln Ser
    2110            2115            2120 cag ccc ggc atg caa ccc cag cct ggc atg cac cag cag ccc agc        7232
Gln Pro Gly Met Gln Pro Gln Pro Gly Met His Gln Gln Pro Ser
    2125            2130            2135 ctg cag aac ctg aat gcc atg cag gct ggc gtg ccg cgg ccc ggt        7277
Leu Gln Asn Leu Asn Ala Met Gln Ala Gly Val Pro Arg Pro Gly
    2140            2145            2150 gtg cct cca cag cag cag gcg atg gga ggc ctg aac ccc cag ggc        7322
Val Pro Pro Gln Gln Gln Ala Met Gly Gly Leu Asn Pro Gln Gly
    2155            2160            2165 cag gcc ttg aac atc atg aac cca gga cac aac ccc aac atg gcg        7367
Gln Ala Leu Asn Ile Met Asn Pro Gly His Asn Pro Asn Met Ala
    2170            2175            2180 agt atg aat cca cag tac cga gaa atg tta cgg agg cag ctg ctg        7412
Ser Met Asn Pro Gln Tyr Arg Glu Met Leu Arg Arg Gln Leu Leu
    2185            2190            2195 cag cag cag cag caa cag cag cag caa caa cag cag caa cag cag        7457
Gln Gln Gln Gln Gln Gln Gln Gln Gln Gln Gln Gln Gln Gln Gln
    2200            2205            2210 cag cag caa ggg agt gcc ggc atg gct ggg ggc atg gcg ggg cac        7502
Gln Gln Gln Gly Ser Ala Gly Met Ala Gly Gly Met Ala Gly His
    2215            2220            2225 ggc cag ttc cag cag cct caa gga ccc gga ggc tac cca ccg gcc        7547
Gly Gln Phe Gln Gln Pro Gln Gly Pro Gly Gly Tyr Pro Pro Ala
    2230            2235            2240 atg cag cag cag cag cgc atg cag cag cat ctc ccc ctc cag ggc        7592
Met Gln Gln Gln Gln Arg Met Gln Gln His Leu Pro Leu Gln Gly
    2245            2250            2255
```

```
agc tcc atg ggc cag atg gcg gct cag atg gga cag ctt ggc cag      7637
Ser Ser Met Gly Gln Met Ala Ala Gln Met Gly Gln Leu Gly Gln
    2260            2265                2270 atg ggg cag ccg ggg ctg ggg gca gac agc acc ccc aac atc cag      7682
Met Gly Gln Pro Gly Leu Gly Ala Asp Ser Thr Pro Asn Ile Gln
2275            2280                2285 caa gcc ctg cag cag cgg att ctg cag caa cag cag atg aag cag      7727
Gln Ala Leu Gln Gln Arg Ile Leu Gln Gln Gln Gln Met Lys Gln
    2290            2295                2300 cag att ggg tcc cca ggc cag ccg aac ccc atg agc ccc cag caa      7772
Gln Ile Gly Ser Pro Gly Gln Pro Asn Pro Met Ser Pro Gln Gln
2305            2310                2315 cac atg ctc tca gga cag cca cag gcc tcg cat ctc cct ggc cag      7817
His Met Leu Ser Gly Gln Pro Gln Ala Ser His Leu Pro Gly Gln
    2320            2325                2330 cag atc gcc acg tcc ctt agt aac cag gtg cgg tct cca gcc cct      7862
Gln Ile Ala Thr Ser Leu Ser Asn Gln Val Arg Ser Pro Ala Pro
2335            2340                2345 gtc cag tct cca cgg ccc cag tcc cag cct cca cat tcc agc ccg      7907
Val Gln Ser Pro Arg Pro Gln Ser Gln Pro Pro His Ser Ser Pro
    2350            2355                2360 tca cca cgg ata cag ccc cag cct tcg cca cac cac gtc tca ccc      7952
Ser Pro Arg Ile Gln Pro Gln Pro Ser Pro His His Val Ser Pro
2365            2370                2375 cag act ggt tcc ccc cac ccc gga ctc gca gtc acc atg gcc agc      7997
Gln Thr Gly Ser Pro His Pro Gly Leu Ala Val Thr Met Ala Ser
    2380            2385                2390 tcc ata gat cag gga cac ttg ggg aac ccc gaa cag agt gca atg      8042
Ser Ile Asp Gln Gly His Leu Gly Asn Pro Glu Gln Ser Ala Met
2395            2400                2405 ctc ccc cag ctg aac acc ccc agc agg agt gcg ctg tcc agc gaa      8087
Leu Pro Gln Leu Asn Thr Pro Ser Arg Ser Ala Leu Ser Ser Glu
    2410            2415                2420 ctg tcc ctg gtc ggg gac acc acg ggg gac acg cta gag aag ttt      8132
Leu Ser Leu Val Gly Asp Thr Thr Gly Asp Thr Leu Glu Lys Phe
2425            2430                2435 gtg gag ggc ttg tag                                              8147
Val Glu Gly Leu
    2440

<210> SEQ ID NO 10
<211> LENGTH: 2442
<212> TYPE: PRT
<213> ORGANISM: human

<400> SEQUENCE: 10

Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
```

-continued

```
                100                 105                 110
Ala Ser Leu Ser Ala Met Gly Lys Ser Pro Leu Ser Gln Gly Asp Ser
            115                 120                 125

Ser Ala Pro Ser Leu Pro Lys Gln Ala Ala Ser Thr Ser Gly Pro Thr
        130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
        275                 280                 285

Gly Ala Thr Gly Val Asn Pro Gln Leu Ala Ser Lys Gln Ser Met Val
    290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
            340                 345                 350

Leu Ile Gln Gln Gln Leu Val Leu Leu Leu His Ala His Lys Cys Gln
        355                 360                 365

Arg Arg Glu Gln Ala Asn Gly Glu Val Arg Ala Cys Ser Leu Pro His
    370                 375                 380

Cys Arg Thr Met Lys Asn Val Leu Asn His Met Thr His Cys Gln Ala
385                 390                 395                 400

Gly Lys Ala Cys Gln Val Ala His Cys Ala Ser Ser Arg Gln Ile Ile
                405                 410                 415

Ser His Trp Lys Asn Cys Thr Arg His Asp Cys Pro Val Cys Leu Pro
            420                 425                 430

Leu Lys Asn Ala Ser Asp Lys Arg Asn Gln Gln Thr Ile Leu Gly Ser
        435                 440                 445

Pro Ala Ser Gly Ile Gln Asn Thr Ile Gly Ser Val Gly Thr Gly Gln
    450                 455                 460

Gln Asn Ala Thr Ser Leu Ser Asn Pro Asn Pro Ile Asp Pro Ser Ser
465                 470                 475                 480

Met Gln Arg Ala Tyr Ala Ala Leu Gly Leu Pro Tyr Met Asn Gln Pro
                485                 490                 495

Gln Thr Gln Leu Gln Pro Gln Val Pro Gly Gln Gln Pro Ala Gln Pro
            500                 505                 510

Gln Thr His Gln Gln Met Arg Thr Leu Asn Pro Leu Gly Asn Asn Pro
        515                 520                 525
```

```
Met Asn Ile Pro Ala Gly Gly Ile Thr Thr Asp Gln Gln Pro Pro Asn
    530                 535                 540

Leu Ile Ser Glu Ser Ala Leu Pro Thr Ser Leu Gly Ala Thr Asn Pro
545                 550                 555                 560

Leu Met Asn Asp Gly Ser Asn Ser Gly Asn Ile Gly Thr Leu Ser Thr
                565                 570                 575

Ile Pro Thr Ala Ala Pro Pro Ser Ser Thr Gly Val Arg Lys Gly Trp
            580                 585                 590

His Glu His Val Thr Gln Asp Leu Arg Ser His Leu Val His Lys Leu
        595                 600                 605

Val Gln Ala Ile Phe Pro Thr Pro Asp Pro Ala Ala Leu Lys Asp Arg
    610                 615                 620

Arg Met Glu Asn Leu Val Ala Tyr Ala Lys Lys Val Glu Gly Asp Met
625                 630                 635                 640

Tyr Glu Ser Ala Asn Ser Arg Asp Glu Tyr Tyr His Leu Leu Ala Glu
                645                 650                 655

Lys Ile Tyr Lys Ile Gln Lys Glu Leu Glu Glu Lys Arg Arg Ser Arg
            660                 665                 670

Leu His Lys Gln Gly Ile Leu Gly Asn Gln Pro Ala Leu Pro Ala Pro
        675                 680                 685

Gly Ala Gln Pro Pro Val Ile Pro Gln Ala Gln Pro Val Arg Pro Pro
    690                 695                 700

Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
                725                 730                 735

Ala Pro Met Gly Pro Arg Ala Ala Ser Pro Met Asn His Ser Val Gln
            740                 745                 750

Met Asn Ser Met Gly Ser Val Pro Gly Met Ala Ile Ser Pro Ser Arg
        755                 760                 765

Met Pro Gln Pro Pro Asn Met Met Gly Ala His Thr Asn Asn Met Met
    770                 775                 780

Ala Gln Ala Pro Ala Gln Ser Gln Phe Leu Pro Gln Asn Gln Phe Pro
785                 790                 795                 800

Ser Ser Ser Gly Ala Met Ser Val Gly Met Gly Gln Pro Pro Ala Gln
                805                 810                 815

Thr Gly Val Ser Gln Gly Gln Val Pro Gly Ala Ala Leu Pro Asn Pro
            820                 825                 830

Leu Asn Met Leu Gly Pro Gln Ala Ser Gln Leu Pro Cys Pro Pro Val
        835                 840                 845

Thr Gln Ser Pro Leu His Pro Thr Pro Pro Ala Ser Thr Ala Ala
    850                 855                 860

Gly Met Pro Ser Leu Gln His Thr Thr Pro Gly Met Thr Pro Pro
865                 870                 875                 880

Gln Pro Ala Ala Pro Thr Gln Pro Ser Thr Pro Val Ser Ser Ser Gly
                885                 890                 895

Gln Thr Pro Thr Pro Thr Pro Gly Ser Val Pro Ser Ala Thr Gln Thr
            900                 905                 910

Gln Ser Thr Pro Thr Val Gln Ala Ala Gln Ala Gln Val Thr Pro
        915                 920                 925

Gln Pro Gln Thr Pro Val Gln Pro Pro Ser Val Ala Thr Pro Gln Ser
930                 935                 940
```

```
Ser Gln Gln Gln Pro Thr Pro Val His Ala Gln Pro Pro Gly Thr Pro
945                 950                 955                 960

Leu Ser Gln Ala Ala Ala Ser Ile Asp Asn Arg Val Pro Thr Pro Ser
            965                 970                 975

Ser Val Ala Ser Ala Glu Thr Asn Ser Gln Gln Pro Gly Pro Asp Val
        980                 985                 990

Pro Val Leu Glu Met Lys Thr Glu Thr Gln Ala Glu Asp Thr Glu Pro
            995                 1000                1005

Asp Pro Gly Glu Ser Lys Gly Glu Pro Arg Ser Glu Met Met Glu
    1010            1015            1020

Glu Asp Leu Gln Gly Ala Ser Gln Val Lys Glu Glu Thr Asp Ile
    1025            1030            1035

Ala Glu Gln Lys Ser Glu Pro Met Glu Val Asp Glu Lys Lys Pro
    1040            1045            1050

Glu Val Lys Val Glu Val Lys Glu Glu Glu Glu Ser Ser Ser Asn
    1055            1060            1065

Gly Thr Ala Ser Gln Ser Thr Ser Pro Ser Gln Pro Arg Lys Lys
    1070            1075            1080

Ile Phe Lys Pro Glu Glu Leu Arg Gln Ala Leu Met Pro Thr Leu
    1085            1090            1095

Glu Ala Leu Tyr Arg Gln Asp Pro Glu Ser Leu Pro Phe Arg Gln
    1100            1105            1110

Pro Val Asp Pro Gln Leu Leu Gly Ile Pro Asp Tyr Phe Asp Ile
    1115            1120            1125

Val Lys Asn Pro Met Asp Leu Ser Thr Ile Lys Arg Lys Leu Asp
    1130            1135            1140

Thr Gly Gln Tyr Gln Glu Pro Trp Gln Tyr Val Asp Asp Val Trp
    1145            1150            1155

Leu Met Phe Asn Asn Ala Trp Leu Tyr Asn Arg Lys Thr Ser Arg
    1160            1165            1170

Val Tyr Lys Phe Cys Ser Lys Leu Ala Glu Val Phe Glu Gln Glu
    1175            1180            1185

Ile Asp Pro Val Met Gln Ser Leu Gly Tyr Cys Cys Gly Arg Lys
    1190            1195            1200

Tyr Glu Phe Ser Pro Gln Thr Leu Cys Cys Tyr Gly Lys Gln Leu
    1205            1210            1215

Cys Thr Ile Pro Arg Asp Ala Ala Tyr Tyr Ser Tyr Gln Asn Arg
    1220            1225            1230

Tyr His Phe Cys Glu Lys Cys Phe Thr Glu Ile Gln Gly Glu Asn
    1235            1240            1245

Val Thr Leu Gly Asp Asp Pro Ser Gln Pro Gln Thr Thr Ile Ser
    1250            1255            1260

Lys Asp Gln Phe Glu Lys Lys Lys Asn Asp Thr Leu Asp Pro Glu
    1265            1270            1275

Pro Phe Val Asp Cys Lys Glu Cys Gly Arg Lys Met His Gln Ile
    1280            1285            1290

Cys Val Leu His Tyr Asp Ile Ile Trp Pro Ser Gly Phe Val Cys
    1295            1300            1305

Asp Asn Cys Leu Lys Lys Thr Gly Arg Pro Arg Lys Glu Asn Lys
    1310            1315            1320

Phe Ser Ala Lys Arg Leu Gln Thr Thr Arg Leu Gly Asn His Leu
    1325            1330            1335

Glu Asp Arg Val Asn Lys Phe Leu Arg Arg Gln Asn His Pro Glu
```

-continued

|  |  |  |  |  |  |  |  |  |  |
|---|---|---|---|---|---|---|---|---|---|
|  | 1340 |  |  | 1345 |  |  | 1350 |  |  |
| Ala | Gly | Glu | Val | Phe | Val | Arg | Val | Val | Ala | Ser | Ser | Asp | Lys | Thr |
| 1355 |  |  |  | 1360 |  |  | 1365 |  |  |
| Val | Glu | Val | Lys | Pro | Gly | Met | Lys | Ser | Arg | Phe | Val | Asp | Ser | Gly |
| 1370 |  |  |  | 1375 |  |  | 1380 |  |  |
| Glu | Met | Ser | Glu | Ser | Phe | Pro | Tyr | Arg | Thr | Lys | Ala | Leu | Phe | Ala |
| 1385 |  |  |  | 1390 |  |  | 1395 |  |  |
| Phe | Glu | Glu | Ile | Asp | Gly | Val | Asp | Val | Cys | Phe | Phe | Gly | Met | His |
| 1400 |  |  |  | 1405 |  |  | 1410 |  |  |
| Val | Gln | Glu | Tyr | Gly | Ser | Asp | Cys | Pro | Pro | Asn | Thr | Arg | Arg |
| 1415 |  |  |  | 1420 |  |  | 1425 |  |  |
| Val | Tyr | Ile | Ser | Tyr | Leu | Asp | Ser | Ile | His | Phe | Arg | Pro | Arg |
| 1430 |  |  |  | 1435 |  |  | 1440 |  |  |
| Cys | Leu | Arg | Thr | Ala | Val | Tyr | His | Glu | Ile | Leu | Ile | Gly | Tyr | Leu |
| 1445 |  |  |  | 1450 |  |  | 1455 |  |  |
| Glu | Tyr | Val | Lys | Lys | Leu | Gly | Tyr | Val | Thr | Gly | His | Ile | Trp | Ala |
| 1460 |  |  |  | 1465 |  |  | 1470 |  |  |
| Cys | Pro | Pro | Ser | Glu | Gly | Asp | Asp | Tyr | Ile | Phe | His | Cys | His | Pro |
| 1475 |  |  |  | 1480 |  |  | 1485 |  |  |
| Pro | Asp | Gln | Lys | Ile | Pro | Lys | Pro | Lys | Arg | Leu | Gln | Glu | Trp | Tyr |
| 1490 |  |  |  | 1495 |  |  | 1500 |  |  |
| Lys | Lys | Met | Leu | Asp | Lys | Ala | Phe | Ala | Glu | Arg | Ile | Ile | His | Asp |
| 1505 |  |  |  | 1510 |  |  | 1515 |  |  |
| Tyr | Lys | Asp | Ile | Phe | Lys | Gln | Ala | Thr | Glu | Asp | Arg | Leu | Thr | Ser |
| 1520 |  |  |  | 1525 |  |  | 1530 |  |  |
| Ala | Lys | Glu | Leu | Pro | Tyr | Phe | Glu | Gly | Asp | Phe | Trp | Pro | Asn | Val |
| 1535 |  |  |  | 1540 |  |  | 1545 |  |  |
| Leu | Glu | Glu | Ser | Ile | Lys | Glu | Leu | Glu | Gln | Glu | Glu | Glu | Glu | Arg |
| 1550 |  |  |  | 1555 |  |  | 1560 |  |  |
| Lys | Lys | Glu | Glu | Ser | Thr | Ala | Ala | Ser | Glu | Thr | Thr | Glu | Gly | Ser |
| 1565 |  |  |  | 1570 |  |  | 1575 |  |  |
| Gln | Gly | Asp | Ser | Lys | Asn | Ala | Lys | Lys | Lys | Asn | Asn | Lys | Lys | Thr |
| 1580 |  |  |  | 1585 |  |  | 1590 |  |  |
| Asn | Lys | Asn | Lys | Ser | Ser | Ile | Ser | Arg | Ala | Asn | Lys | Lys | Pro |
| 1595 |  |  |  | 1600 |  |  | 1605 |  |  |
| Ser | Met | Pro | Asn | Val | Ser | Asn | Asp | Leu | Ser | Gln | Lys | Leu | Tyr | Ala |
| 1610 |  |  |  | 1615 |  |  | 1620 |  |  |
| Thr | Met | Glu | Lys | His | Lys | Glu | Val | Phe | Phe | Val | Ile | His | Leu | His |
| 1625 |  |  |  | 1630 |  |  | 1635 |  |  |
| Ala | Gly | Pro | Val | Ile | Asn | Thr | Leu | Pro | Pro | Ile | Val | Asp | Pro | Asp |
| 1640 |  |  |  | 1645 |  |  | 1650 |  |  |
| Pro | Leu | Leu | Ser | Cys | Asp | Leu | Met | Asp | Gly | Arg | Asp | Ala | Phe | Leu |
| 1655 |  |  |  | 1660 |  |  | 1665 |  |  |
| Thr | Leu | Ala | Arg | Asp | Lys | His | Trp | Glu | Phe | Ser | Ser | Leu | Arg | Arg |
| 1670 |  |  |  | 1675 |  |  | 1680 |  |  |
| Ser | Lys | Trp | Ser | Thr | Leu | Cys | Met | Leu | Val | Glu | Leu | His | Thr | Gln |
| 1685 |  |  |  | 1690 |  |  | 1695 |  |  |
| Gly | Gln | Asp | Arg | Phe | Val | Tyr | Thr | Cys | Asn | Glu | Cys | Lys | His | His |
| 1700 |  |  |  | 1705 |  |  | 1710 |  |  |
| Val | Glu | Thr | Arg | Trp | His | Cys | Thr | Val | Cys | Glu | Asp | Tyr | Asp | Leu |
| 1715 |  |  |  | 1720 |  |  | 1725 |  |  |
| Cys | Ile | Asn | Cys | Tyr | Asn | Thr | Lys | Ser | His | Ala | His | Lys | Met | Val |
| 1730 |  |  |  | 1735 |  |  | 1740 |  |  |

-continued

```
Lys Trp Gly Leu Gly Leu Asp Asp Glu Gly Ser Ser Gln Gly Glu
1745                1750                1755

Pro Gln Ser Lys Ser Pro Gln Glu Ser Arg Arg Leu Ser Ile Gln
    1760                1765                1770

Arg Cys Ile Gln Ser Leu Val His Ala Cys Gln Cys Arg Asn Ala
1775                1780                1785

Asn Cys Ser Leu Pro Ser Cys Gln Lys Met Lys Arg Val Val Gln
1790                1795                1800

His Thr Lys Gly Cys Lys Arg Lys Thr Asn Gly Gly Cys Pro Val
1805                1810                1815

Cys Lys Gln Leu Ile Ala Leu Cys Cys Tyr His Ala Lys His Cys
1820                1825                1830

Gln Glu Asn Lys Cys Pro Val Pro Phe Cys Leu Asn Ile Lys His
1835                1840                1845

Lys Leu Arg Gln Gln Ile Gln His Arg Leu Gln Gln Ala Gln
1850                1855                1860

Leu Met Arg Arg Arg Met Ala Thr Met Asn Thr Arg Asn Val Pro
1865                1870                1875

Gln Gln Ser Leu Pro Ser Pro Thr Ser Ala Pro Pro Gly Thr Pro
1880                1885                1890

Thr Gln Gln Pro Ser Thr Pro Gln Thr Pro Gln Pro Pro Ala Gln
1895                1900                1905

Pro Gln Pro Ser Pro Val Ser Met Ser Pro Ala Gly Phe Pro Ser
1910                1915                1920

Val Ala Arg Thr Gln Pro Pro Thr Thr Val Ser Thr Gly Lys Pro
1925                1930                1935

Thr Ser Gln Val Pro Ala Pro Pro Pro Pro Ala Gln Pro Pro Pro
1940                1945                1950

Ala Ala Val Glu Ala Ala Arg Gln Ile Glu Arg Glu Ala Gln Gln
1955                1960                1965

Gln Gln His Leu Tyr Arg Val Asn Ile Asn Asn Ser Met Pro Pro
1970                1975                1980

Gly Arg Thr Gly Met Gly Thr Pro Gly Ser Gln Met Ala Pro Val
1985                1990                1995

Ser Leu Asn Val Pro Arg Pro Asn Gln Val Ser Gly Pro Val Met
2000                2005                2010

Pro Ser Met Pro Pro Gly Gln Trp Gln Gln Ala Pro Leu Pro Gln
2015                2020                2025

Gln Gln Pro Met Pro Gly Leu Pro Arg Pro Val Ile Ser Met Gln
2030                2035                2040

Ala Gln Ala Ala Val Ala Gly Pro Arg Met Pro Ser Val Gln Pro
2045                2050                2055

Pro Arg Ser Ile Ser Pro Ser Ala Leu Gln Asp Leu Leu Arg Thr
2060                2065                2070

Leu Lys Ser Pro Ser Ser Pro Gln Gln Gln Gln Gln Val Leu Asn
2075                2080                2085

Ile Leu Lys Ser Asn Pro Gln Leu Met Ala Ala Phe Ile Lys Gln
2090                2095                2100

Arg Thr Ala Lys Tyr Val Ala Asn Gln Pro Gly Met Gln Pro Gln
2105                2110                2115

Pro Gly Leu Gln Ser Gln Pro Gly Met Gln Pro Gln Pro Gly Met
2120                2125                2130
```

-continued

```
His Gln Gln Pro Ser Leu Gln Asn Leu Asn Ala Met Gln Ala Gly
    2135            2140            2145

Val Pro Arg Pro Gly Val Pro Pro Gln Gln Ala Met Gly Gly
    2150            2155            2160

Leu Asn Pro Gln Gly Gln Ala Leu Asn Ile Met Asn Pro Gly His
    2165            2170            2175

Asn Pro Asn Met Ala Ser Met Asn Pro Gln Tyr Arg Glu Met Leu
    2180            2185            2190

Arg Arg Gln Leu Leu Gln Gln Gln Gln Gln Gln Gln Gln Gln Gln
    2195            2200            2205

Gln Gln Gln Gln Gln Gln Gln Gly Ser Ala Gly Met Ala Gly
    2210            2215            2220

Gly Met Ala Gly His Gly Gln Phe Gln Gln Pro Gln Gly Pro Gly
    2225            2230            2235

Gly Tyr Pro Pro Ala Met Gln Gln Gln Gln Arg Met Gln Gln His
    2240            2245            2250

Leu Pro Leu Gln Gly Ser Ser Met Gly Gln Met Ala Ala Gln Met
    2255            2260            2265

Gly Gln Leu Gly Gln Met Gly Gln Pro Gly Leu Gly Ala Asp Ser
    2270            2275            2280

Thr Pro Asn Ile Gln Gln Ala Leu Gln Gln Arg Ile Leu Gln Gln
    2285            2290            2295

Gln Gln Met Lys Gln Gln Ile Gly Ser Pro Gly Gln Pro Asn Pro
    2300            2305            2310

Met Ser Pro Gln Gln His Met Leu Ser Gly Gln Pro Gln Ala Ser
    2315            2320            2325

His Leu Pro Gly Gln Gln Ile Ala Thr Ser Leu Ser Asn Gln Val
    2330            2335            2340

Arg Ser Pro Ala Pro Val Gln Ser Pro Arg Pro Gln Ser Gln Pro
    2345            2350            2355

Pro His Ser Ser Pro Ser Pro Arg Ile Gln Pro Gln Pro Ser Pro
    2360            2365            2370

His His Val Ser Pro Gln Thr Gly Ser Pro His Pro Gly Leu Ala
    2375            2380            2385

Val Thr Met Ala Ser Ser Ile Asp Gln Gly His Leu Gly Asn Pro
    2390            2395            2400

Glu Gln Ser Ala Met Leu Pro Gln Leu Asn Thr Pro Ser Arg Ser
    2405            2410            2415

Ala Leu Ser Ser Glu Leu Ser Leu Val Gly Asp Thr Thr Gly Asp
    2420            2425            2430

Thr Leu Glu Lys Phe Val Glu Gly Leu
    2435            2440
```

METHOD FOR IDENTIFYING OR SCREENING AGONIST AND ANTAGONIST TO PPAR

This is a continuation of application Ser. No. 09/514,247, filed Feb. 28, 2000, now issued as U.S. Pat. No. 6,365,361, which is a continuation-in-part application of PCT application No. PCT/JP98/03734, filed Aug. 24, 1998.

BACKGROUND OF THE INVENTION

1. Technical Field

This invention relates to a novel method for identifying or screening an agonist for and/or antagonist to peroxisome proliferator activated receptor (PPAR).

2. Background Art

Peroxisome, an organelle found in the cells of animals and plants, contains a group of enzymes participating in the lipometabolism and absorption of lipids such as cholesterol. An increase in peroxisome is also induced by diet or physiological factors. It is known that a group of chemicals diversified in structure including antilipemic (fibrates), insecticides and plasticizers such as phthalic acids when they are administered dramatically increase the size and number of peroxisome in liver and kidney and at the same time elevate the ability of metabolizing fatty acids in peroxisome through intermediary of an increase in the expression of enzymes necessary for the β-oxidation cycle. Hence, they are called peroxisome proliferator. Among studies on the mechanism of such a peroxisome proliferation, a nuclear receptor that is activated by the group of chemicals has been identified and named peroxisome proliferator activated receptor (PPAR).

From its structure, etc., PPAR is considered to be a member of nuclear receptor (nuclear hormone receptor) super family. Like other nuclear receptors, it is activated by its binding to a ligand, and its binding to a response sequence (PPRE: peroxisome proliferator response element) existing upstream of a target gene domain activates transcription of the target gene. PPAR is known to form a heterodimer with a retinoid X receptor (RXR) and binds to PPRE in the form of the heterodimer. Also, like other nuclear receptors, PPAR is considered to have the interaction with a group of transcription coactivators (coactivators) in order to exhibit its transcription activation activity.

Hitherto, three kinds of PPAR subtypes called PPARα, PPARδ (or NUC-1, PPARβ, FAAR) and PPARδ have been identified and their genes (cDNA) have been cloned (Lemberger et al., Annu. Rev. Cell. Dev. Biol., vol. 12, pp. 335–363, 1996). Of the three kinds, PPARδ is expressed particularly in an adipose tissue and considered to be a factor that closely participates in differentiation of adipocytes (Tontonoz et al., Genes and Development, vol. 8, pp. 1224–1234, 1994; Tontonoz et al., Cell, vol. 79, pp. 1147–1156, 1994).

On the other hand, various thiazolidinedione derivatives show hypoglycemic effect in a model animal of non-insulin-dependent diabetes mellitus (NIDDM) and are expected as a NIDDM remedy having an insulin resistance releasing effect. These thiazolidinedione derivatives act as ligands to PPARγ and specifically activate PPARγ, which has been discovered in recent studies (Lehmann et al., Journal of Biological Chemistry, vol. 270, pp. 12953–12956, 1995). Since a strong correlation is observed between such a PPARγ activation ability of thiazolidinedione derivatives and the hypoglycemic effect in a hereditary obese mouse, PPARγ is considered to be a target molecule of the pharmaceutical effect of the thiazolidinedione derivatives (Willson et al., Journal of Medicinal Chemistry, vol. 39, pp. 665–668, 1996). This also relates to the fact that an adipose tissue where PPARγ is specifically expressed is an organ that plays an important role in maintaining energy balance. From these findings, a compound specifically acting as an agonist for PPARγ is considered to be very useful as a remedy for diabetes mellitus.

However, to date, those methods known as screening methods for PPAR acting agents each involve the problems that operation is complicated and simultaneous treatment of multiple samples is difficult.

For example, there has been known a method for examining PPAR activation ability of a sample using animal cells having introduced therein reporter plasmid containing a reporter gene linked to a PPAR expression vector and a PPAR response element (PPRE), with using as an index a change in the amount of expression of a reporter gene in the cells (WO 96/22884, Tontonoz et al., Genes and Development, vol. 8, pp. 1224–1234, 1994). As its improved method, there has been known a method using animal cells having introduced therein vector for expressing fused protein in which the DNA binding domain of GAL4, i.e., the transcription factor of yeast, and the ligand binding domain of PPAR linked together, along with having introduced a reporter plasmid containing a reporter gene linked to the response element of GAL4 (GAL4 binding element) (WO 96/33724, Lehmann et al., Journal of Biological Chemistry, vol. 270, pp. 12953–12956, 1995; Willson et al., Journal of Medicinal Chemistry, vol. 39, pp. 665–668, 1996). In these methods, an extrinsic gene is introduced into animal cells. Upon the introduction of gene, it is sometimes the case that the integration of a gene into a chromosome has taken place, the gene is influenced by the site where the gene is integrated. Therefore, it is necessary to use a transformed cell in which gene is not influenced by the chromosome. To acquire such a transformed animal cell and express an extrinsic gene stably are accompanied by technical difficulties. Since coactivators, RXR, etc. derived from host animal are considered to participate in the activation of transcription in these methods, there is the possibility that the action of the test substance to PPAR alone cannot be detected surely.

As a method for directly detecting the binding between PPAR and a ligand without using any animal cell or reporter gene, there has been known a method for examining binding and antagonism between a fused protein comprising the ligand binding domain of PPAR and glutathione-S-transferase (GST) and a test compound labeled with a radioisotope (Willson et al., Journal of Medicinal Chemistry, vol. 39, pp. 665–668, 1996; Buckle et al., Bioorganic & Medical Chemistry Letters, vol. 6, pp. 2121–2126, 1996). Recently, it has been elucidated that like other nuclear receptor RXR, etc., PPAR interacts with SRC-1, one of coactivators, ligand-dependently. Based on this finding, Krey et al. reported a method for detecting the action of a test compound as a ligand using a fused protein comprising the ligand binding domain of PPAR and glutathione-S-transferase (GST) and SRC-1 labeled with a radioisotope (Krey et al., Molecular Endocrinology, Vol. 11, pp. 779–791, 1997). However, these methods each use a label of radioisotope and therefore it is accompanied by a danger and has a limitation in treating power since preparation of a labeled compound or coactivator on a large scale is difficult.

As described above, upon screening PPAR acting agents, a screening method which is simple, high precision, and efficient has been desired.

An object of this invention is to provide a novel method for identifying and screening an agonist and/or antagonist to peroxisome proliferator activated receptor (PPAR).

The present inventors have uniquely found that in addition to SRC-1, one of the coactivators, that is already known to interact with PPAR, CBP (CREB-binding protein) interacts with PPAR ligand-dependently and identified the binding domain of the coactivator to PPAR. Further, based on these findings, they have completed a method for identifying or screening a novel PPAR acting agent that detects a ligand-dependent interaction between PPAR and a coactivator using a Two-hybrid system of yeast.

SUMMARY OF THE INVENTION

This invention relates to a method for identifying or screening an agonist for or antagonist to a peroxisome proliferator-activated receptor (PPAR), which comprises allowing a test cell and a substance to be tested to coexist, and detecting a change in a ligand-dependent interaction between the PPAR and a coactivator in the test cells due to the substance to be tested by measuring the expression of a reporter gene as an index.

DESCRIPTION OF THE PREFERRED EMBODIMENTS

Figure 1A:
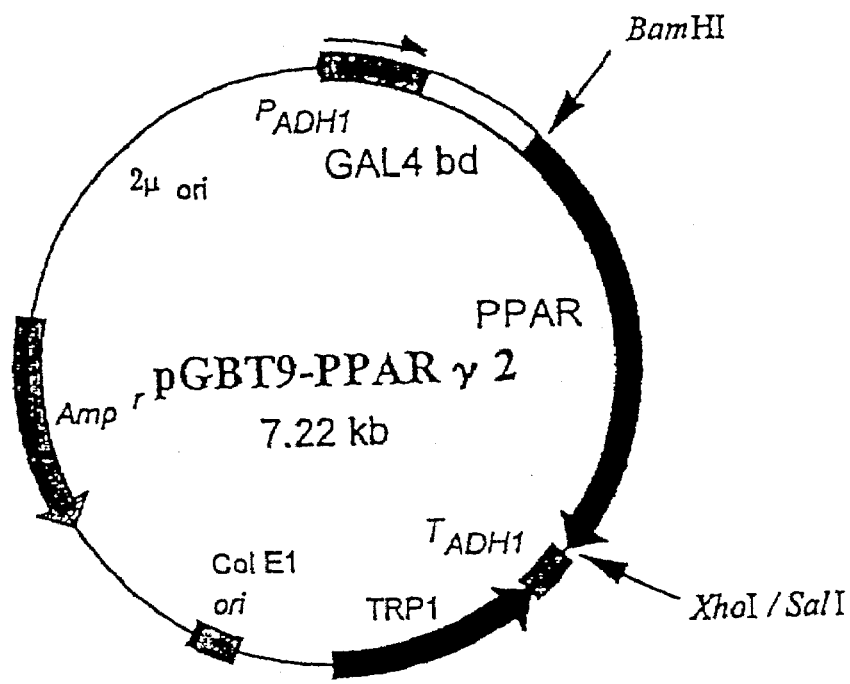
FIGS. 1A and 1B are schematic diagrams illustrating the constitutions of used plasmids pGBT9-PPARγ2 (FIG. 1A) and pGAD424-CBP (FIG. 1B).

In this invention, a ligand-dependent interaction between PPAR and a coactivator in the test cells is detected. PPAR changes its conformation into an activated type by binding to a ligand and the interaction with a coactivator takes place. That is, the ligand-dependent interaction is the binding of PPAR with the coactivator promoted in the presence of a ligand of PPAR.

As PPAR, subtypes such as PPARα, PPARδ (or NUC-1, PPARβ, FAAR) and PPARγ are known. In this invention, any one of these subtypes can be used. Among these, PPARγ is a target molecule of thiazolindinedione derivatives having an antidiabetic effect. A method for identifying or screening a specifically acting agent therefor is useful in research and development of a remedy for diabetes mellitus.

PPAR may be derived from any species so far as it is identified as the same molecular species and exhibits its function in the organism as a nuclear receptor. For example, it includes those derived from mammalians such as human, mouse, rat, hamster, etc., and in addition those derived from clawed toad (*Xenopus laevis*). From the point of view of utilizing research and development of a remedy for humans, it is preferred to use human-derived one out of these.

The gene sequences and amino acid sequences of PPARα (Dreyer et al., Cell, vol. 68, pp. 879–887, 1992, Green et al., Nature, vol. 347, pp. 645–650, 1990, Goettlicher et al., Proc. Natl. Acad. Sci. USA, vol. 89, pp. 4653–4657, 1992), PPARδ (or NUC-1, PPARβ, FFAR) (Dreyer et al., Cell, vol. 68, pp. 879–887, 1992, Kliewer et al., Proc. Natl. Acad. Sci. USA, vol. 91, pp. 7355–7359, 1994, Amri et al., Journal of Biological Chemistry, vol. 270, pp. 2367–2371, 1995, Xing et al., Biochem. Biophys. Res. Commun., vol. 217, pp. 1015–1025, 1995) and PPARγ (Dreyer et al., Cell, vol. 68, p. 879–887, 1992, Zhu et al., Journal of Biological Chemistry, vol. 268, pp. 26817–26820, 1993, Kliewer et al., Proc. Natl. Acad. Sci., USA, vol. 91, pp. 7355–7359, 1994, Mukherjee et al., Journal of Biological Chemistry, vol. 272, pp. 8071–8076, 1997, Elbrecht et al., Biochem. Biophys. Res. Commun., vol. 224, pp. 431–437, 1996, Chem et al., Biochem. Biophys. Res. Commun., vol. 196, pp. 671–677, 1993, Tontonoz et al., Genes & Development, vol. 8, pp. 1224–1234, 1994, Aperlo et al., Gene, vol. 162, pp. 297–302, 1995) have already been reported. PPARγ includes two kinds of isoforms, PPARγ1 and PPARγ2. PPARγ1 as compared with PPARγ2 is deleted of 30 amino acids on the N-terminal side but the other amino acid sequence is quite the same. Each is expressed in an adipose tissue.

Among the reports, presuming from the homology with other nuclear receptor, etc., the ligand binding domain (LBD) of PPAR is considered to correspond to the domain including about No. 167 to 463 amino acids from the N-terminal side in the case of PPARα, to the domain including about No. 133 to 440 amino acids from the N-terminal side in the case of PPARδ, and the domain including about No. 174 to 475 amino acids from the N-terminal side in the case of PPARγ (corresponding to about residues 174 to 475 of SEQ ID NO:6)

To detect the interaction between PPAR and coactivator, a polypeptide including at least the ligand binding domain may be used. Cut and use of a polypeptide including the ligand binding domain of PPAR can exclude nonspecific interaction and hence are preferred.

The coactivator used in this invention may be any one so far as it interacts with PPAR ligand-dependently, that is, the interaction with PPAR in the presence of a ligand of PPAR is promoted. The coactivator which is considered to interact with nuclear receptor includes, for example, CBP, SRC-1, RIP140 (Cavailles et al., EMBO Journal, vol. 14, pp. 3741–3751, 1995), TIF1 (Douarin et al., EMBO Journal, vol. 14, pp. 2020–2033, 1995, Vom Baur et al., EMBO Journal, vol. 15, pp. 110–124, 1996), TIF2 (Voegel et al., EMBO Journal, vol. 15, pp. 3667–3675, 1996), SUG1 (Vom Baur et al., EMBO Journal, vol. 15, pp. 110–124 , 1996), P300 (Chakravarti et al., Nature, vol. 383, pp. 99–103, 1996), etc. These are expected to interact also with PPAR ligand-dependently. The coactivator which is considered to interact specifically with PPARδ includes, for example, PGC-1 (PPAR gamma coactivator-1) (Puigserver et al., Cell, vol. 92, pp. 829–839, 1998), PGC-2 (PPAR gamma coactivator-2) (Cactillo et al., EMBO Journal, vol. 18, pp. 3676–3687, 1999), etc. These are expected to interact with PPARδ ligand-dependently.

Among these, CBP and SRC-1, as shown in Examples in the present specification later on and in the report by Krey et al., have been confirmed to interact with PPAR and can be used advantageously in this invention.

CBP (CREB-binding protein) is a protein that has been originally identified as a coactivator of transcription factor CREB (cAMP-regulated enhancer binding protein) that binds to ORE (cAMP-regulated enhancer) and both gene (SEQ ID NO:7 for mouse and SEQ ID NO:9 for human) and amino acid (SEQ ID NO:8 for mouse and SEQ ID NO:10 for human) sequences thereof have been known (Chrivia et al. Nature, vol., 365, pp. 855–859, 1993; Kwok et al., Nature, vol. 370, pp. 223–226). Recently, it has been revealed that CBP binds not only to CREB but also to a nuclear receptor in the presence of a ligand to serve as a coactivator and that the N-terminal moiety of CBP participates in the interaction with the nuclear receptor (Kamei et al., Cell, vol. 85, pp. 403–414, 1995). That the N-terminal moiety of CBP interacts also with PPARγ ligand-dependently was found uniquely by the present inventors.

SRC-1 is known to interact with nuclear receptors such as glucocorticoid receptor, estrogen receptor, thyroid hormone receptor and retinoid X receptor (RXR) ligand-dependently and serves as a coactivator. Its gene and amino acid sequence are also known (Onate et al., Science, vol. 270, pp. 1354–1357, 1995). In the Krey et al. report (Molecular Endocrinology, vol. 11, pp. 779–791, 1997), the experiment using the ligand binding domain of clawed toad (Xenopus laevis)-derived PPAR and RI-labeled SRC-1 indicated that PPAR also interacts with SRC-1 ligand-dependently.

Upon detecting the ligand-dependent interaction with PPAR, the whole coactivator may be used, besides, a polypeptide that contains at least PPAR binding domain (the domain that participates in binding to PPAR) may be used. Coactivators generally have large molecular weights and use of the whole sometimes result in difficulty of expression of protein and it is preferred that appropriate domain be selected and used from this point of view.

The PPAR binding domain (domain participating in binding to PPAR) of a coactivator can be guessed from information on the position of its binding domain with a nuclear receptor if such an information has been reported. Also, using a system for detecting protein-protein interaction (for example, two-hybrid system of yeast), presence or absence of the interaction of a certain domain with PPAR may be examined and selection of a proper domain may be made. In the case where the coactivator is CBP, then PPAR binding domain exists near the N-terminal moiety (domain including about No. 1 to 450 amino acids).

In the present invention, the ligand-dependent interaction between PPAR and coactivator is detected in test cells using the expression of a reporter gene as an index and measurement was made of a change in the interaction due to the substance to be tested.

Noticing the interaction between PPAR and coactivator, the transcription activation effect of PPAR per se is not detected, so that various factors inherent to mammals participating in the expression of transcription activation ability of PPAR do not have to be present. Therefore, there is no need to use mammalian cells as test cells. Cells may be any one so far as they are eucaryotic cells. For example, there may be mentioned yeast cells, insect cells, mammalian cells, etc. Among these, yeast cells are advantageous in that their cultivation is easy and can be performed quickly and that application of genetic recombination technique such as introduction of extrinsic genes is easy. As yeast cells, there can be used cell lines of microbes belonging to the genera *Saccharomyces, Schizosaccharomyces*, etc., such as *Saccharomyces cerevisiae, Schizosaccharomyces pombe*, etc.

As the test cells, usually those that contain extrinsic PPAR and coactivators may be used. Use of cells containing no intrinsic PPAR or coactivators interacting therewith is preferred since the influence due to intrinsic elements can be excluded.

The change in the interaction between PPAR and coactivator due to the substance to be tested can be efficiently measured by a method utilizing a two-hybrid system.

The two-hybrid system is a method for detecting protein-protein interaction using the expression of a reporter gene as a marker (U.S. Pat. No. 5,283,173 and Proc. Natl. Acad. Sci., USA, vol. 88, pp. 9578–9582, 1991). Many transcription factors can be divided into two domains having different functions, that is, a DNA binding domain and a transcriptional activation domain. In the two-hybrid system, for example, to examine the interaction between the two proteins X and Y, two kinds of fused protein, that is, a fused protein composed of the DNA binding domain of a transcription factor and X, and a fused protein composed of the transcriptional activation domain of a transcription factor and Y are simultaneously expressed in yeast cells. When the proteins X and Y interact with each other, the two kinds of fused proteins form by combination a transcription complex exhibiting a single function as a whole. This transcription complex combines with a response element (the site of DNA to which a transcription factor is bound specifically) in the nuclei of cells and activates transcription of a reporter gene positioned downstream. Thus, the interaction between the two proteins can be detected by the expression of the reporter gene (for example, the enzyme activity of gene products).

The two-hybrid system can usually be used in the identification of unknown proteins that interact with a specific protein and generally used in qualitative evaluation of protein-protein interaction. The present inventors utilized this system, and thus, completed a method which can quantitatively measure the ligand-dependent interaction between PPAR and a coactivator, and can be applied to the identification or screening of antagonist/agonist for receptors, in which quantitative evaluation is indispensable As one embodiment of the present invention, there may be mentioned a method for identifying an agonist for or an antagonist to PPAR, comprising: using test cells containing (i) a first fused gene coding for a first fused protein comprising at least ligand binding domain of PPAR and a first domain of a transcription factor, wherein the first domain of said transcription factor being a DNA binding domain or a transcriptional activation domain;

(ii) a second fused gene coding for a second fused protein comprising at least PPAR binding domain of a coactivator which interacts with the PPAR and a second domain of the transcription factor, wherein the second domain of said transcription factor is a transcriptional activation domain when the first domain of the transcription factor is a DNA binding domain or is a DNA binding domain when the first domain of the transcription factor is a transcriptional activation domain, and (iii) a response element to which the DNA binding domain of said transcription factor can bind and a reporter gene linked thereto, making the test cells coexist with a substance to be tested, and detecting, by measuring the expression of a reporter gene as an index, a change in the ligand-dependent interaction between the peroxisome proliferator-activated receptor (PPAR) and a coactivator in the test cells occurring due to the substance to be tested.

In this embodiment, the transcription factor used for detecting the interaction between the PPAR and coactivator is not limited particularly so long as it is a transcription factor (other than PPAR) of eucaryotic organism that can exhibit the function of transcriptional activation in cells. However, it is preferred to use a transcription factor derived from yeast from the viewpoint that it does not need the coactivator, etc.; derived from mammalian cells to function and it independently exhibits transcriptional activation ability efficiently in yeast cells.

Such a transcription factor includes yeast GAL4 protein (Keegan et al., Science, vol. 231, pp. 699–704, 1986, Ma et al., Cell, vol. 48, pp. 847–853, 1987), GCN4 protein (Hope et al., Cell, vol. 46, pp. 885–894, 1986), ADR1 protein (Thukral et al., Molecular and Cellular Biology, vol. 9, pp. 2360–2369, 1989), etc.

The DNA binding domain of the transcription factor may be those having a DNA binding ability to the response element but alone having no transcriptional activation ability. Also, the transcriptional activation domain of the transcription factor may be those having a transcriptional activation ability but alone having no DNA binding ability to the response element.

The DNA binding domain and transcriptional activation domain of a transcription factor, in the case of, for example, GAL4, are known to be present on the N-terminal side (a domain including about No. 1 to 147 amino acids) and C-terminal side (the domain including about No. 768 to 881 amino acids), respectively. In the case of GCN4, they are known to be present on the C-terminal side (the domain including about No. 228 to 265 amino acids) and N-terminal side (the domain including about No. 107 to 125 amino acids), respectively. In the case of ADR1, they are known to be present on the N-terminal side (the domain including about No. 76 to 172 amino acids) and the C-terminal side (the domain including about No. 250 to 1323 amino acids), respectively.

As the response element, a response element corresponding to a transcription factor may be used and DNA sequences to which the DNA binding domain of the transcription factor can bind are used. The response element corresponding to a transcription factor generally exists in a domain upstream of the gene whose transcriptional activity is controlled by the transcription factor, so that such a domain may be cut out for use. If its sequence is known, corresponding oligonucleotide may be synthesized by chemical synthesis and used.

For example, in case of GAL4 is used as a transcription factor, GAL4-specific DNA sequence called UASg (upstream activation site of galactose genes) may be used as the response element. UASg is contained in the domain upstream of galactose metabolism genes such as the GAL1 gene, etc., so that these domains may be used. Alternatively, a nucleotide sequence corresponding to UASg may be chemically synthesized and used.

The reporter gene positioned downstream of the response element is not limited particularly so far as it is a commonly used one and it is preferred to use the gene of an enzyme which is stable and allows easy quantitative measurement of its activity, etc. Such a reporter gene includes, for example, β-galactosidase gene (lacZ) derived from *E. coli*, chloramphenicol acetyltransferase gene (CAT) derived from bacterial transposone, luciferase gene (Luc) derived from a firefly, etc. Among these, *E. coli*-derived β-galactosidase gene (lacZ) is preferable since it can be readily measured with visible light using a coloring substrate. The reporter gene may be a gene having an original promoter of the gene, or besides, a gene of which promoter Dart is replaced with one derived from of another gene may be used. The reporter gene may be enough if it is operatively linked downstream of the response element.

The first fused protein contains the ligand binding domain of PPAR and the first domain of the transcription factor (DNA binding domain or transcriptional activation domain) and the second fused protein contains the PPAR binding domain of a coactivator and the second domain of transcription factor (transcriptional activation domain or DNA binding domain). The two kinds of domains constituting the fused protein may be each arranged in the upstream domain. The fused protein may have additional construction or deletion or substitution of sequence within the range that necessary functions are not damaged.

The first and second domains of the transcription factor must be integrated before they can bind to the response element and play the function of activating gene transcription. For this purpose, when the first domain is a DNA binding domain, the second domain must be a transcriptional activation domain. When the first domain is a transcriptional activation domain, the second domain must be a DNA binding domain. The first and second domains do not necessarily be derived from the same transcription factor but may be derived from different transcription factors.

The fused genes coding for the first and second fused proteins may be designed and constructed by using a usual genetic recombination technique. As for the DNA coding for the ligand binding domain of PPAR, PPAR binding domain of a coactivator, DNA binding domain of a transcription factor and transcriptional activation domain of a transcription factor constituting the first and second fused proteins, cDNA may be isolated from cDNA library by, for example, screening, etc., using PCR (Polymerase Chain Reaction) or a synthetic probe which uses a primer or probe designed and synthesized based on the information on the known amino acid sequence or nucleotide sequence. DNAs coding for the respective domains are linked and the resulting material is linked downstream of a suitable promoter to construct a fused gene. To each domain or DNA coding this, it may be introduced addition, deletion, substitution of sequence within the range where necessary functions are not damaged.

The resulting first and second fused genes may be incorporated into a suitable vector plasmid and introduced into host cells in the form of a plasmid. The first and second fused genes may be constructed so as to be contained on the same plasmid or on separate plasmids.

The response element and the reporter gene linked thereto may also be designed, constructed using usual genetic recombination technique and the construction is incorporated into the vector plasmid, and the resulting recombinant plasmid may be introduced into host cells. Alternatively, cells in which such a construction is incorporated in chromosomal DNA may be acquired and used.

Test cells including all the constitution may be acquired, for example, by introducing one or more plasmids containing the first and second fused genes into host cells in which a response element along with a reporter gene linked thereto are introduced into the chromosomal DNA of the host cells.

The thus obtained test cells are cultivated, for example, in the presence of a substance to be tested, and an interaction between PPAR and a coactivator is detected and measured by the expression of the reporter gene. When the substance to be tested binds to PPAR and an interaction with the coactivator occurs depending on the binding, an increase in the reporter activity is observed. Such a substance to be tested can be identified as an agonist for PPAR. For example, when the substance to be tested binds to PPAR but does not promote the interaction with the coactivator, addition of it together with true ligand or the drug identified as an agonist, a decrease in the reporter activity expressed by the true ligand or agonist is observed. Such a substance to be tested is identified as an antagonist to PPAR.

Of the invention, as another embodiment of the method in which the ligand-dependent interaction with CBP is detected and the effect of a substance to be tested is measured with respect to said interaction, there is, for example, a method in which the ligand-dependent interaction between PPAR and CBP is measured directly. In this method, for example, CBP or its PPAR binding domain labeled with RI, etc. is used and the binding with a fused protein composed of a suitable tag protein, such as glutathione-S-transferase (GST), protein A, β-galactosidase, and maltose-binding protein (MBP), and the ligand binding domain of PPAR is directly detected in the presence of the substance to be tested.

According to the method of the invention, for example, screening for an acting agent against PPARγ can be performed. As the ligand for PPARγ, various types of thiazolidinedione derivatives have been identified and prostaglandin, 15d-PGJ$_2$ (15-deoxy-$\Delta^{12,14}$-prostaglandin J$_2$), one of arachidonic acid metabolites, is considered to be a true ligand (Cell, vol. 83, pp. 803–812 and pp. 813–819, 1995). Therefore, upon the identification or screening of an agonist for PPARγ, 15d-PGJ$_2$ can be used as a positive control. By examining presence or absence of inhibition against ligand-dependent interaction expressed by 15d-PGJ$_2$, the identification or screening of antagonist to PPARγ can be practiced.

The agonist for PPARγ is expected as a remedy for treating diabetes having excellent hypoglycemic effect. Since PPARγ is an inducing factor for differentiation of adipocytes, the antagonist to PPARγ is expected to have effect as an anti-obese agent.

Upon screening PPARγ acting agents, the effect on other subtypes, that is, PPARα or PPARδ (or NTJC-1, PPARβ, FAAR) is inspected, whereby medicines having a high selectivity for PPARγ can be selected.

EXAMPLES

In the following, the invention will be explained in more detail by referring to Examples. However, the present invention is not limited thereto.

In the following examples, unless otherwise specified particularly, each operation was according to the method described in "Molecular Cloning" (written by Sambrook, J., Fritsch, E. F. and Maniatis, T., published by Cold Spring Harbor laboratory Press in 1988) was followed, or when commercially available reagent or kit was used, they were used according to the commercially available specification.

Example 1

Construction of PPARγ Acting Agent Screening System Based on Ligand-dependent Interaction Between PPARγ and CBP (1) Isolation of Genes of PPARγ2 and CBP cDNA of PPARγ2 was acquired from cDNA library (available from Clontech Co.) By the PCR method. In the PCR, the following primers of SEQ ID NOs: 1 and 2 in the Sequence Listing shown below were used. These primers were designed based on the gene sequence of human PPARγ2 described in Accession No. D83233 (SEQ ID NO:5) of gene database, Genbank, and a restriction enzyme recognition site for inserting into yeast expression vector was added to the terminal of the primer. The resulting 1574 base pair fragment had a SmaI recognition site before the start codon and a XhoI recognition site after the stop codon, thus coding for full-length human PPARγ2.

The cDNA at the N terminus of CBP was obtained by the PCR method from cDNA obtained by reverse transcription reaction from RNA prepared from mouse adipocytes. In the PCR, the primers shown in SEQ. ID. NOs: 3 and 4 in the Sequence Listing shown below were used. These primers were designed based on the gene sequence of mouse CBP described in the literature by Chrivia et al. (Nature, vol. 365, 855–859, 1993) to the termini of the primer being added a restriction enzyme recognition site for insertion into yeast expression vector. The resulting 1411 base pair fragment had a BamHI recognition site before the start codon and a BglII recognition site at the C terminus, and coding for the No. 1 to 464 amino acids of mouse CBP.

(2) Construction of Expression Vector for Fused Protein Comprising Ligand Binding Domain of PPARγ and DNA Binding Domain of GAL4

The 1574 base pair fragment containing PPARγ2 gene obtained in (1) above was cleaved at the XhoI recognition site designed at the terminus and the BamHI recognition site in the base sequence. The fragments obtained were inserted into the BamHI-SalI site of yeast expression vector pGBT9 (available from Clontech Co., vector for yeast two hybrid system) containing the gene of the DNA binding domain of transcription factor GAL4 (No. 1 to 147 amino acid residues of GAL4). As a result, plasmid pGBT9-PPARγ2 (FIG. 1A) for expressing a fused protein comprising the portion downstream of the No. 181 amino acid residue of human PPARγ2 (ligand binding domain) and the DNA binding domain of GAL4 was obtained. In FIG. 1A, GAL4 bd stands for a GAL4 DNA binding domain sequence, $^P$ADH1 stands for alcohol dehydrogenase gene promoter, $^T$ADH1 stands for an alcohol dehydrogenase gene terminator, Amp$^r$ stands for an ampicillin resistant gene, ColE1 ori stands for a collicin E1 replication start point, and 2 μ ori stands for a 2 μ replication start point.

(3) Construction of Expression Vector for Fused Protein Comprising the N-terminal Domain of CBP (PPAR binding domain) and the Transcriptional Activation Domain of GAL4

Figure 1B:
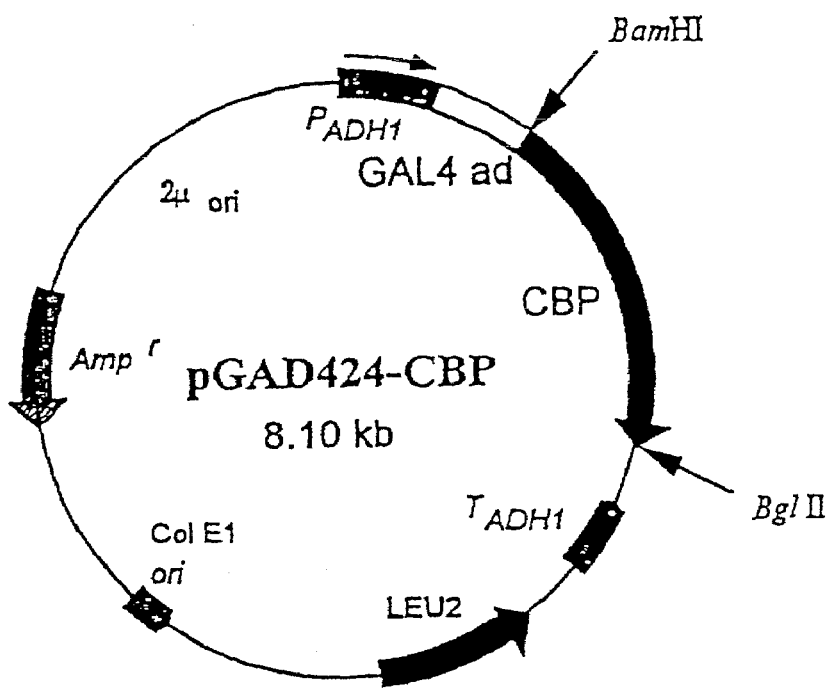

The 1411 base pair fragment containing CBP gene obtained in (1) above (N-terminal domain) was cleaved at the BamHI recognition site and BglII recognition site designed at the termini. The fragments obtained were inserted into the BamHI-BglII site of yeast expression vector pGAD424 (available from Clontech Co., vector for yeast two hybrid system) containing the gene of the transcriptional activation domain of GAL4 (No. 768 to 881 amino acid residues of GAL4). As a result, plasmid pGAD424-CBP (FIG. 1B) for expressing a fused protein comprising the portion of the No. 1 to 464 amino acid residues of mouse CBP (N-terminal domain) and the transcriptional activation domain of GAL4 was obtained. In FIG. 1B, GAL4 ad stands for GAL4 transcriptional activation domain sequence and others have the same meanings as in FIG. 1A.

(4) Transformation of Yeast

Using yeast cell strain SFY526 (available from Clontech Co.), the fused protein expression plasmids pGBT9-PPARγ2 and pGAD424-CBP obtained in (2) and (3) above were introduced therein. The cell strain SFY526 (genotype was MATa, ura3-52, his3-200, ade2-101, lys2-801, trp1-901, leu2-3, 112, canr, gal4-542, gal80-538, URA3::GAL1-lacZ) had incorporated in the chromosome a fused gene of GAL1 and lacZ and is a cell strain having deletion mutation relative to GAL4 gene (Bartel et al., Bio Techniques, vol. 14, pp. 920–924, 1993). The transformation was performed by the lithium acetate method and incubated in a synthetic medium depleted of tryptophan and leucine which are selection markers for the respective plasmids to perform screening to obtain a transformant in which only one of the plasmids was introduced and a transformant in which the both plasmids were introduced.

(5) Detection of Ligand-dependent Interaction Between PPARγ and CBP

The yeast transformant containing both of the plasmids pGBT9-PPARγ and pGAD424-CBP or the yeast transformant containing only one of the plasmids was cultivated in YPD medium (liquid medium). Upon cultivation, 15-deoxy-$\Delta^{12,14}$-prostaglandin $J_2$, which is a ligand of PPARγ2 in a living body, diluted with YPD medium was added (or not added). 15-deoxy-$\Delta^{12,14}$-prostaglandin $J_2$ (hereinafter abbreviated to as "15d-$PGJ_2$") used was commercially available (available from CAYMAN CHEMICALS, CO., U.S.A.). The cultivation was performed for 4 to 5 hours. After the cultivation, the yeast cells were recovered by centrifugation and β-galactosidase activity was measured.

Figure 2A:
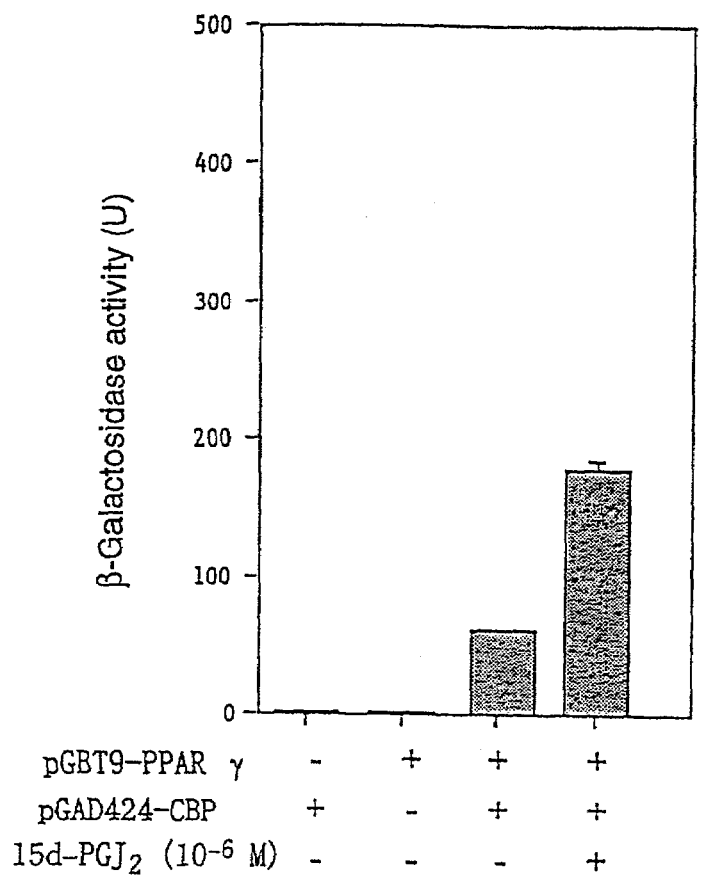
FIGS. 2A and 2B are graphs illustrating ligand-dependent interaction between PPARγ and CBP in the presence or absence of $10^{-6}$M 15d-PCJ$_2$ (FIG. 2A) or with varying concentrations of 15d-PCJ$_2$ (FIG. 2B).
Figure 2B:
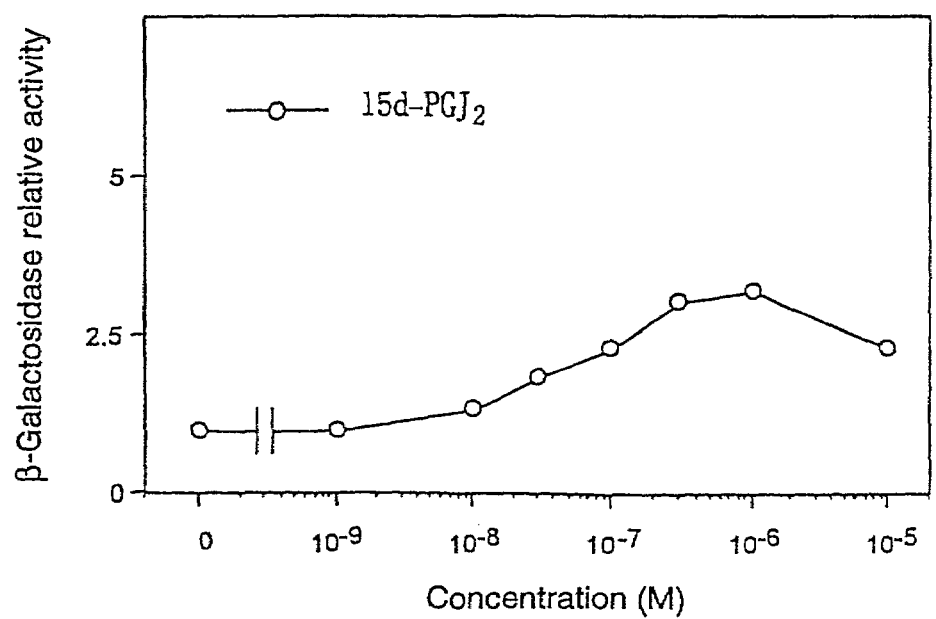

As a result, by the addition of 15d-$PGJ_2$, an increase in β-galactosidase activity (lacZ gene expression) in yeast containing both of the plasmids pGBT-PPARγ and pGAD424-CBP was observed (FIG. 2A). Such an increase in β-galactosidase activity due to 15d-$PGJ_2$ was observed dependent on the concentration of 15d-$PGJ_2$ (FIG. 2B). These were considered to be attributable to the ligand-dependent interaction between PPARγ and CBP due to the presence of the ligand, 15d-$PGJ_2$. From this result, it revealed that the N-terminal domain of CBP interacts with PPAR. Further, it was considered that in this system, the ligand-dependent interaction between PPARγ and CBP could be detected and measured.

Next, using as a substance to be tested thiazolidine-dione derivative T-174 (chemical name: 5-[[2-(2-naphthalenylmethyl)-5-benzoxazolyl]methyl]-2,4-thiazolidinedione) represented by the following formula:

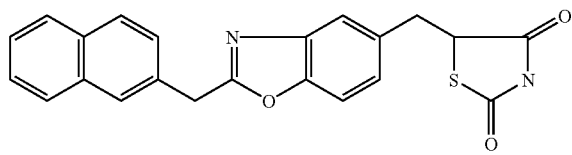

its effect on PPARγ was examined.

In the same manner as mentioned above, the yeast transformant containing both of the plasmids pGBT9-PPARγ and pGAD424-CBP or a yeast transformant containing only one of the plasmids was cultivated. However, upon cultivation, T-174 was added as a substance to be tested instead of 15d-$PGJ_2$ in the medium. T-174 used was synthesized by a method similar to that described in Japanese Provisional Patent Publication No. 56675/1989 (Example 49).

Figure 3A:
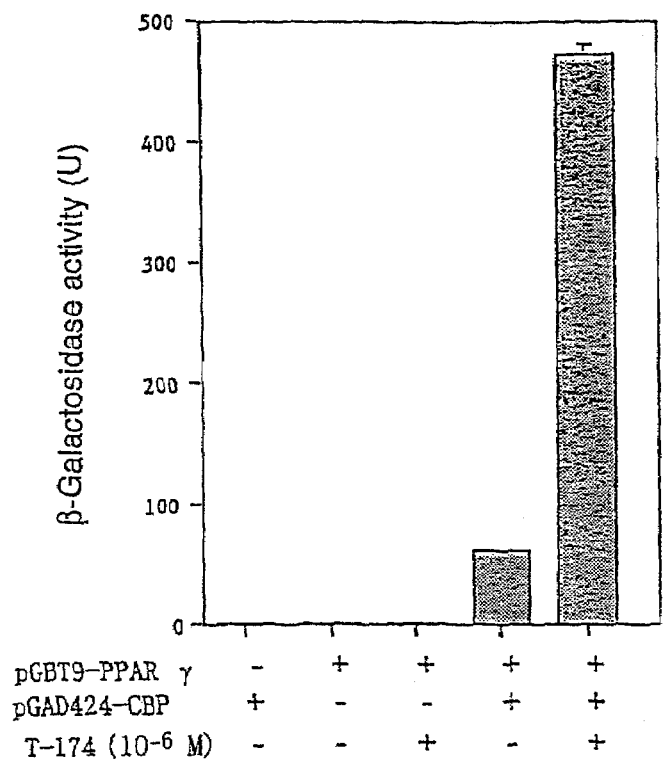
FIGS. 3A and 3B are graphs illustrating action of T-174 to the interaction between PPARγ and CBP in the presence of $10^{-6}$M T-174 (FIG. 3A) or with varying concentrations of T-174 (FIG. 3B).
Figure 3B:
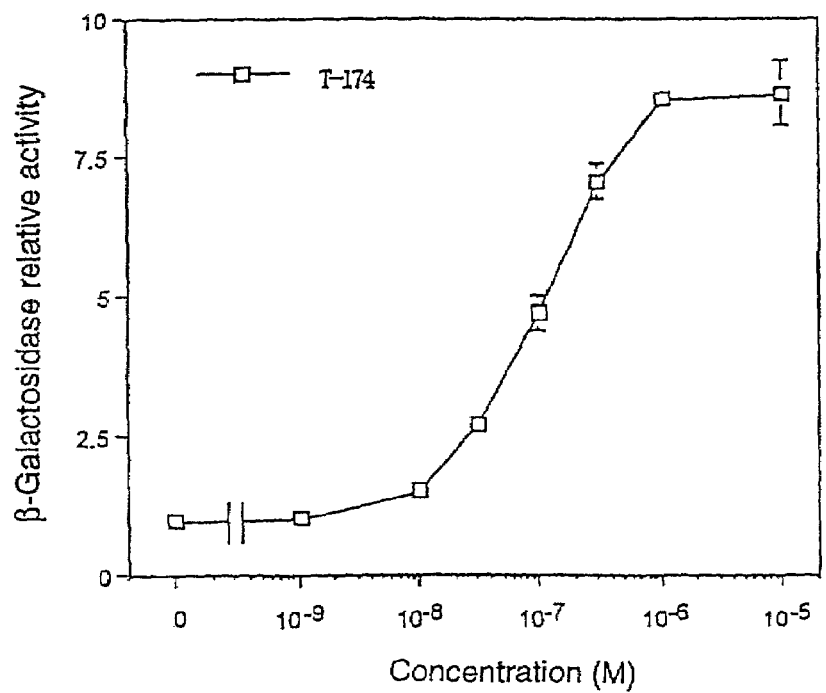

As a result, an increase in β-galactosidase activity was observed only in the yeast containing both of the plasmids pGBT-PPARγ and pGAD424-CBP (FIG. 3A). Its effect was dependent on the concentration of T-174 (FIG. 3B). Thus, the ligand-dependent interaction between PPARγ and CBP was detected due to the presence of T-174, so that T-174 was identified as an agonist acting as a ligand to PPARγ.

T-174 is known to have a hypoglycemic effect in a disease model of mouse (KK-Ay mouse) (Japanese Provisional Patent Publications No. 56675/1989 and No. 167225/1990). Although its acting point was unclear, the above results indicate that the acting target molecule of T-174 is PPARγ.

Example 2

Construction of PPARγ Acting Agent Screening System Based on the Ligand-dependent Interaction Between PPARγ and SRC-1 cDNA of the full domain of SRC-1 is obtained by the PCR method from the cDNA library prepared from human adipose tissue. The primers are designed based on the gene sequence of human SRC-1 described in the literature of Onate et al. (Science, vol. 270, pp. 1354–1357, 1995) and to the terminus of the primer is added a restriction enzyme recognition site for insertion of yeast expression vector.

This is used instead of the cDNA of CBP and, in the same manner as in Example 1 (2) and (3), the cDNA of PPARγ2 is inserted into the yeast expression vector pGBT9 and the cDNA of SRC-1 is inserted into the yeast expression vector pGAD424, respectively, whereby an expression vector for a fused protein comprising the ligand binding domain of PPARγ and the DNA binding domain of CAL4, and an expression vector a fused protein comprising the full domain of SRC-1 and the transcriptional activation domain of GAL4 are constructed.

The resultant two kinds of fused protein expression plasmid are introduced into yeast cell strain SFY526 of which a fused gene of GAL1 and lacZ is incorporated in its chromosome and having a deletion mutation regarding GAL4 gene in the same manner as in Example (4) above.

Using the obtained transformed strain, the ligand-dependent interaction between PPARγ and SRC-1 is detected in the same manner as in Example (5) above.

INDUSTRIAL APPLICABILITY

The conventional identification method for PPAR acting agent detecting the transcriptional activation ability of PPAR in the cells accepts participation of a coactivator and RXR which are intrinsic to the cells. The method of this invention is free from this participation, so that only the effect of the substance to be tested to PPAR can be detected with accuracy. Also, the method of the invention does not have to use mammalian cells and can use yeast cells as well, so that cultivation operations can be performed with ease and quickly. Further, there is no need for using radioisotope-labeled compound to be tested or protein and hence the method is safe and simple.

According to the method of the invention, since it is possible to treat a number of substances to be tested simultaneously with sufficient sensitivity and quantitativeness, the identification and screening of agonist for and antagonist to PPAR can be performed efficiently.

The invention claimed is:

1. A method for identifying or screening an agonist for, or an antagonist to, human peroxisome proliferator-activated receptor γ (PPARγ), characterized by detecting a ligand-dependent interaction between human PPARγ and CREB-binding protein (CBP), and measuring the effect of a substance to be tested on said interaction, wherein the effect of the substance is determined as follows:

i) when the ligand-dependent interaction between PPARγ and CBP occurs in the presence of the substance tested, then the substance is identified or selected as an agonist for PPARγ; and ii) when the interaction between PPARγ and CBP that occurs in the presence of a true ligand or an agonist is inhibited by the existence of the substance tested, then the substance is identified or selected as an antagonist for PPARγ.

2. The method of claim 1, wherein the interaction between a ligand binding domain of the human PPARγ and a nuclear receptor binding domain of the CBP is detected.

3. The method of claim 2, wherein the ligand binding domain of human PPARγ comprises residues 174 to 475 of SEQ ID NO:6.

4. The method of claim 2, wherein human PPARγ comprises the amino acid sequence of SEQ ID NO:6.

5. The method of claim 1, wherein the CBP has the amino acid sequence of SEQ ID NO:8.

6. The method of claim 1, wherein the CBP has the amino acid sequence of SEQ ID NO:10.

7. The method of claim 1, which is for identifying or screening an agonist for human PPARγ.

8. The method of claim 1, which is for identifying or screening an antagonist for human PPARγ.

9. The method of claim 8, wherein 15-deoxy-$\Delta^{12,14}$-prostaglandin $J_2$(15d-PGJ$_2$) is used as a true ligand or an agonist.

* * * * *